United States Patent [19]

Reff et al.

[11] Patent Number: 5,998,144
[45] Date of Patent: *Dec. 7, 1999

[54] METHOD FOR INTEGRATING GENES AT SPECIFIC SITES IN MAMMALIAN CELLS VIA HOMOLOGOUS RECOMBINATION AND VECTORS FOR ACCOMPLISHING THE SAME

[75] Inventors: Mitchell R. Reff, San Diego; Richard Spence Barnett, San Marcos; Karen Retta McLachlan, Solana Beach, all of Calif.

[73] Assignee: Idec Pharmaceuticals Corporation, San Diego, Calif.

[*] Notice: This patent is subject to a terminal disclaimer.

[21] Appl. No.: 09/023,715

[22] Filed: Feb. 13, 1998

Related U.S. Application Data

[63] Continuation-in-part of application No. 08/819,866, Mar. 14, 1997, Pat. No. 5,830,698.

[51] Int. Cl.$^6$ ............. C12Q 1/68; C12N 15/64; C12N 15/63; C12N 5/10
[52] U.S. Cl. ............. 435/6; 435/91.41; 435/320.1; 435/325; 435/455; 435/463; 536/23.5; 536/23.7; 536/23.72
[58] Field of Search .................. 435/69.1, 91.4, 435/172.3, 320.16, 91.41, 325, 455, 463; 536/23.5, 23.7, 23.72, 23.53

[56] References Cited

PUBLICATIONS

Thomas et al. High frequency targeting of genes to specific sited in the mammalian genome. Cell vol. 44 pp. 419–428, 1986.

*Primary Examiner*—John S. Brusca
*Attorney, Agent, or Firm*—Burns, Doane, Swecker & Mathis, L.L.P.

[57] ABSTRACT

A method for achieving site specific integration of a desired DNA at a target site in a mammalian cell via homologous recombination is described. This method provides for the reproducible selection of cell lines wherein a desired DNA is integrated at a predetermined transcriptionally active site previously marked with a marker plasmid. The method is particularly suitable for the production of mammalian cell lines which secrete mammalian proteins at high levels, in particular immunoglobulins. Novel vectors and vector combinations for use in the subject cloning method are also provided.

45 Claims, 31 Drawing Sheets

DESMOND

HD = Salmonella HisD Gene
N3 = Neomycin Phosphotransferase Exon 3
D = Murine Dihydrofolate reductase
E = Cytomegalovirus and SV40 Enhancers
SA = Splice acceptor
BT = Mouse Beta Globin Major Promoter
B = Bovine Growth Hormone Polyadenylation
S = SV40 Early Polyadenylation
SV = SV40 Late Polyadenylation Desmond
14,683 bp Bst1107 I linear

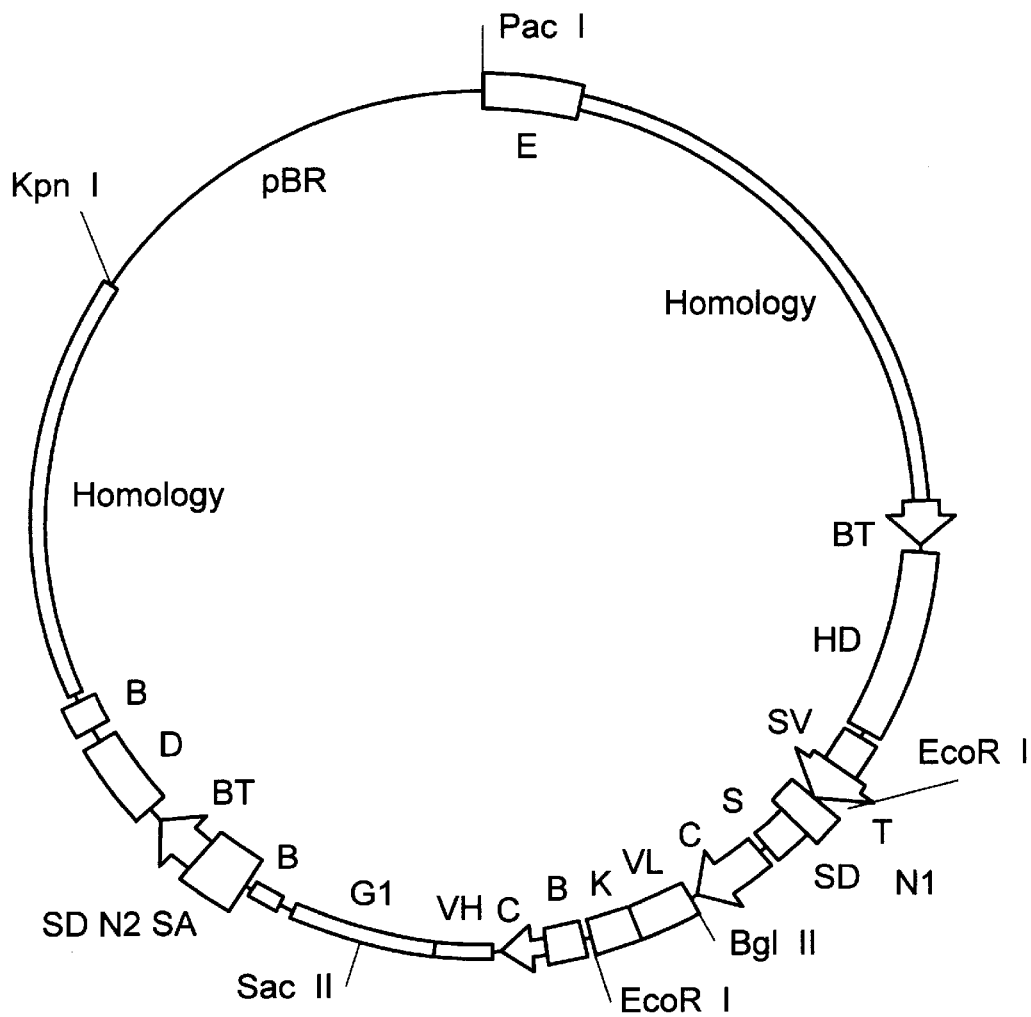

FIG. 2A
Molly

- D = Dihydrofolate reductase
- N1 + Neomycin Phosphotransferase Exon 1
- N2 + Neomycin Phosphotransferase Exon 2
- VL = Anti-CD20 Light chain leader + Variable
- K = Human Kappa Constant
- VH = Anti-CD20 Heavy chain Leader + Variable
- G1 = Human Gamma 1 Constant
- HD = Salmonella Histidinol Dehydrogenase
- E = CMV and SV40 enhancers    S = SV40 Origin
- SD = Splice donor    SA = Splice acceptor
- C = CMV promoter/enhancer
- T = HSV TK promoter and Poloma enhancers
- BT = Mouse Beta Globin Major Promoter
- SV = SV40 Late Polyadenylation
- B = Bovine Growth Hormone Polyadenylation

Southern Analysis of Desmond Marked CHO Cells

FIG. 7A

```
TTTCTAGACC TAGGGCGGGCC AGCTAGTAGC TTTGCTTCTC AATTTCTTAT TTGCATAATG
                                                                60
AGAAAAAAAG GAAAATTAAT TTTAACACCA ATTCAGTAGT TGATTGAGCA AATGCGTTGC
                                                               120
CAAAAAGGAT GCTTTAGAGA CAGTGTTCTC TGCACAGATA AGGACAAACA TTATTCAGAG
                                                               180
GGAGTACCCA GAGCTGAGAC TCCTAAGCCA GTGAGTGGCA CAGCATTCTA GGGAGAAATA
                                                               240
TGCTTGTCAT CACCGAAGCC TGATTCCGTA GAGCCACACC TTGGTAAGGG CCAATCTGCT
                                                               300
CACACAGGAT AGAGAGGGCA GGAGCCAGGG CAGAGCATAT AAGGTGAGGT AGGATCAGTT
                                                               360
GCTCCTCACA TTTGCTTCTG ACATAGTTGT GTTGGGAGCT TGGATAGCTT GGACAGCTCA
                                                               420
GGGCTGCGAT TTCGCGCCAA ACTTGACGGC AATCCTAGCG TGAAGGCTGG TAGGATTTTA
                                                               480
TCCCCGCTGC CATCATGGTT CGACCATTGA ACTGCATCGT CGCCGTGTCC CAAAATATGG
                                                               540
GGATTGGCAA GAACGGAGAC CTACCCTGGC CTCCGCTCAG GAACGAGTTC AAGTACTTCC
                                                               600
AAAGAATGAC CACAACCTCT TCAGTGGAAG GTAAACAGAA TCTGGTGATT ATGGGTAGGA
                                                               660
```

FIG. 7B

```
AAACCTGGTT CTCCATTCCT GAGAAGAATC GACCTTTAAA GGACAGAATT AATATAGTTC
                                                                720
TCAGTAGAGA ACTCAAAGAA CCACCACGAG GAGCTCATTT TCTTGCCAAA AGTTTGGATG
                                                                780
ATGCCTTAAG ACTTATTGAA CAACCGGAAT TGGCAAGTAA AGTAGACATG GTTTGGATAG
                                                                840
TCGGAGGCAG TTCTGTTTAC CAGGAAGCCA TGAATCAACC AGGCCACCTT AGACTCTTTG
                                                                900
TGACAAGGAT CATGCAGGAA TTTGAAAGTG ACACGTTTTT CCCAGAAATT GATTGGGGA
                                                                960
AATATAAACT TCTCCCAGAA TACCCAGGCG TCCTCTCTGA GGTCCAGGAG GAAAAAGGCA
                                                                1020
TCAAGTATAA GTTTGAAGTC TACGAGAAGA AAGACTAACA GGAAGATGCT TTCAAGTTCT
                                                                1080
CTGCTCCCCT CCTAAAGCTA TGCATTTTTA TAAGACCATG GGACTTTTGC TGGCTTTAGA
                                                                1140
TCAGCCTCGA CTGTGCCTTC TAGTTGCCAG CCATCTGTTG TTTGCCCCTC CCCGTGCCT
                                                                1200
TCCTTGACCC TGGAAGGTGC CACTCCCACT GTCCTTTCCT AATAAAATGA GGAAATTGCA
                                                                1260
TCGCATTGTC TGAGTAGGTG TCATTCTATT CTGGGGGGTG GGGTGGGGCA GGACAGCAAG
                                                                1320
```

FIG. 7C

```
GGGGAGGATT GGGAAGACAA TAGCAGGCAT GCTGGGGATG CGGTGGGCTC TATGGAACCA
                                                                1380
GCTGGGGCTC GAAGCGGCCG CCCATTTCGC TGGTGGTCAG ATGCGGGATG GCGTGGGACG
                                                                1440
CGGCGGGGAC CGTCACACTG AGGTTTCCG CCAGACGCCA CTGCTGCCAG GCGCTGATGT
                                                                1500
GCCCGGCTTC TGACCATGCG GTCGCGTTCG GGTAGTTCAG GCAGTTCAAT CAACTGTTTA CCTTGTGGAG
                                                                1560
GCCCGGGCGT CTCCGGCTGC CGCTTGCTA GCGGCTTACC ATCCAGCGCC ACCATCCAGT
                                                                1620
CGACATCCAG AGGCACTTCA CCGCTTGCTA GCGGCTTACC ATCCAGCGCC ACCATCCAGT
                                                                1680
GCAGGAGCTC GTTATCGCTA TGACGGAACA GGTATTCGCT GGTGTTTGC GGTCACTTCG ATGGTTTGCC
                                                                1740
CGGATAAACG GAACTGGAAA AACTGCTGCT GGTGTTTGC TTCCGTCAGC GCTGGATGCG
                                                                1800
GCGTGCGGTC GGCAAAGACC AGACCGTTCA GACCGTTCA GCCGATCGTTC GGCGTATCAC
                                                                1860
CAAAATCACC GCCGTAAGCC GACCACGGGT TGCCGTTTTC ATCATATTTA ATCAGCGACT
                                                                1920
GATCCACCCA GTCCCAGACG AAGCCGCCCT GTAAACGGGG ATACTGACGA AACGCCTGCC
                                                                1980
```

FIG. 7D

```
AGTATTTAGC GAAACCGCCA AGACTGTTAC CCATCGCGTG GGCGTATTCG CAAAGGATCA
                                                                2040
GCGGGCGCGT CTCTCCGGGT AGCGAAAGCC ATTTTTGAT GGACCATTTC GGACCAGCCG
                                                                2100
GGAAGGGCTG GTCTTCATCC ACGCGCGCGT ACATCGGGCA AATAATATCG GTGGCCGTGG
                                                                2160
TGTCGGCTCC GCCGCCTTCA TACTGCACCG GGCGGGAAGG ATCGACAGAT TTGATCCAGC
                                                                2220
GATACAGCGC GTCGTGATTA GCGCCCGTGGC CTGATTCATT CCCCAGCCGAC CAGATGATCA
                                                                2280
CACTCGGGTG ATTACGATCG CGCTGCACCA TTCGCGTTAC GCGTTCGCTC ATCGCCGGTA
                                                                2340
GCCAGCGCGG ATCATCGGTC AGACGATTCA TTGGCACCAT GCCGTGGGTT TCAATATTGG
                                                                2400
CTTCATCCAC CACATACAGG CCGTAGCGGT CGCACAGCGT GTACCACAGC GGATGGTTCG
                                                                2460
GATAATGCGA ACAGCGCACG GCGTTAAAGT TGTTCTGCTT CATCAGCAGG ATATCCTGCA
                                                                2520
CCATCGTCTG CTCATCCATG ACCTGACCAT GCAGAGGATG ATGCTCGTGA CGGTTAACGC
                                                                2580
CTCGAATCAG CAACGGCTTG CCGTTCAGCA GCAGCAGACC ATTTCCAATC CGCACCCTCGC
                                                                2640
```

FIG. 7E

```
GGAAACCGAC ATCGCAGGCT TCTGCTTCAA TCAGCGTGCC GTCGGGCGGTG TGCAGTTCAA   2700
CCACCGCACG ATAGAGATTC GGGATTTCGG CGCTCCACAG TTTCGGGTTT TCGACGTTCA   2760
GACGCAGTGT GACGCGATCG GCATAACCAC CAGGCTCATC GATAATTTCA CCGCCGAAAG   2820
GCGCGGTGCC GCTGGGCGAC TGCGTTTCAC CCTGCCATAA AGAAACTGTT ACCCGTAGGT   2880
AGTCACGCAA CTCGCCGCAC ATCTGAACTT CAGCCTCCAG TACAGCGCGG CTGAAATCAT   2940
CATTAAAGCG AGTGGCAACA TGGAAATCGC TGATTTGTGT AGTCGGTTTA TGCAGCAACG   3000
AGACGTCACG GAAAATGCCG CTCATCCCGCC ACATATCCTG ATCTTCCAGA TAACTGCCGT   3060
CACTCCAACG CAGCACCATC ACCGGCGAGGC GGTTTCTCC GGCGCGGTAAA AATGCGCTCA   3120
GGTCAAATTC AGACGGGCAAA CGACTGTCCT GGCTGTAACC GACCCACGCC CCGTTGCACC   3180
ACAGATGAAA CGCCGAGTTA ACGCCATCAA AAATAATTCG CGTCTGGCCT TCCTGTAGCC   3240
AGCTTTCATC AACATTAAAT GTGAGCGAGT AACAACCCGT CGGATTCTCC GTGGGAACAA   3300
```

FIG. 7F

```
ACGGCGGGATT GACCGTAATG GGATAGGTTA CGTTGGTGTA GATGGGGCGCA TCGTAACCGT
                                                                3360
GCATCTGCCA GTTTGAGGGG ACGACGACAG TATCGGCCTC AGGAAGATCG CACTCCAGCC
                                                                3420
AGCTTTCCGG CACTGCTTCT GGTGCCGGAA ACCAGGCAAA GCGCCATTCG CCATTCAGGC
                                                                3480
TGCGCAACTG TTGGGAAGGG CGATCGGTGC GGGCCTCTTC GCTATTACGC CAGCTGGCGA
                                                                3540
AAGCGGGATG TGCTGCAAGG CGATTAAGTT GGGTAACGCC AGGGTTTTCC CAGTCACGAC
                                                                3600
GTTGTAAAAC GACTTAATCC GTCGAGGGGC TGCCCTCGAAG CAGACGACCT TCCGTTGTGC
                                                                3660
AGCCAGCGGGC GCCTGCGCCG GTGCCCACAA TCGTGCGGCGA ACAAACTAAA CCAGAACAAA
                                                                3720
TCATACCGGC GGCACCGCCG CCACCACCTT CTCCTGTGCC GCGCCCTCCAC
                                                                3780
CACTACCACC ACCATCGATG TCTGAATTGC CGCCCGCTCC ACCAATGCCG ACGGAACCTC
                                                                3840
AACCCGCTGC ACCTTTAGAC GACAGACAAC AATTGTTGGA AGCTATTAGA AACGAAAAAA
                                                                3900
ATCGCACTCG TCTCAGACCG GCTCTCTTAA GGTAGCTCAA ACCAAAAACG GCGCCCGAAA
                                                                3960
```

FIG. 7G

```
CCAGTACAAT AGTTGAGGTG CCGACTGTGT TGCCTAAAGA GACATTGAG CTTAAACCGC
                                                              4020
CGTCTGCACC ACCGCCACCA CCTCCGCCTC CGCCTCCGCC GCCAGCCCCG CCTGCGCCTC
                                                              4080
CACCGATGGT AGATTCATCA TCAGCTCCAC CACCGCCGCC ATTAGTAGAT TGCCGTCTG
                                                              4140
AAATGTTACC ACCGCCCTGCA CCATCGCTTT CTAACGTGTT GTCTGAATTA AAATCGGGCA
                                                              4200
CAGTTAGATT GAAACCCGCC CAAAAACGCC CGCAATCAGA AATAATTCCA AAAAGCTCAA
                                                              4260
CTACAAATTT GATCGCGGGAC GTGTTAGCCG ACACAATTAA TAGGCGTCGT GTGGCTATGG
                                                              4320
CAAAATCGTC TTCGGAAGCA ACTTCTAACG ACGAGGGTTG GGACGACGAC GATAATCGGC
                                                              4380
CTAATAAAGC TAACACGCCC GATGTTAAAT ATGTCCAAGC TACTAGTGGT ACCTTAATTA
                                                              4440
AGGGGCGGAG AATGGGGCGGA ACTGGGCGGGA GTTAGGGGCG GGATGGGGCG AGTTAGGGGC
                                                              4500
GGGACTATGG TTGCTGACTA ATTGAGATGC ATGCTTTGCA TACTTCTGCC TGCTGGGGAG
                                                              4560
CCTGGGGACT TTCCACACCT GGTTGCTGAC TAATTGAGAT GCATGCTTTG CATACTTCTG
                                                              4620
```

FIG. 7H

```
CCTGCTGGGG AGCCTGGGGA CTTTCCACAC CCTAACTGAC ACACATTCCA CAGAATTAAT   4680
TCCCTAGTT  ATTAATAGTA ATCAATTACG GGGTCATTAG TTCATAGCCC ATATATGGAG   4740
TTCCGCGTTA CATAACTTAC GGTAAATGGC CCGCCTGGCT GACCGCTCAA CGACCCCCGC   4800
CCATTGACGT CAATAATGAC GTATGTTCCC ATAGTAACGC CAATAGGGAC TTTCCATTGA   4860
CGTCAATGGG TGGACTATTT ACGGTAAACT GCCCACTTGG CAGTACATCA AGTGTATCAT   4920
ATGCCAAGTA CGCCCCCTAT TGACGTCAAT GACGGTAAAT GGCCCGCCTG GCATTATGCC   4980
CAGTACATGA CCTTATGGGA CTTTCCTACT TGGCAGTACA TCTACGTATT AGTCATCGCT   5040
ATTACCATGG TGATGCGGTT TTGGCAGTAC ATCAATGGGC GTGGATAGCG GTTTGACTCA   5100
CGGGGATTTC CAAGTCTCCA CCCCATTGAC GTCAATGGGA GTTTGTTTTG AAGCTTGGCC   5160
GGCCATATAA ACGGCGGCCA GCTTTATTTA ACGTGTTTAC GTCGAGTCAA TTGTACACTA   5220
ACGACAGTGA TGAAAGAAAT ACAAAAGCGC ATAATATTTT GAACGACGTC GAACCTTTAT   5280
```

FIG. 7I

```
TACAAAACAA AACACAAACG AATATCGACA AAGCTAGATT GCTGCTACAA GATTGGCAA
                                                                5340
GTTTGTGGGC GTTGAGCGAA AATCCATTAG ATAGTCCAGC CATCGGTTCG GAAAAACAAC
                                                                5400
CCTGTTTGA AACTAATCGA AACCTATTTT ACAAATCTAT TGAGGATTTA ATATTTAAAT
                                                                5460
TCAGATATAA AGACGCTGAA AATCATTTGA TTTTCGCTCT AACATACCAC CCTAAAGATT
                                                                5520
ATAAATTTAA TGAATTATTA AAATACATCA GCAACTATAT ATTGATAGAC ATTTCCAGTT
                                                                5580
TGTGATATTA GTTTGTGCGT CTCATTACAA TGGCTGTTAT TTTTAACAAC AAACAACTGC
                                                                5640
TCGCAGACAA TAGTATAGAA AAGGGAGGTG AACTGTTTTT GTTTAACGGT TCGTACAACA
                                                                5700
TTTTGGAAAG TTATGTTAAT CCGGTGCTGC TAAAAAATGG TGTAATTGAA CTAGAAGAAG
                                                                5760
CTGCCGTACTA TGCCGGCAAC ATATTGTACA AAACCGACGA TCCCAAATTC ATTGATTATA
                                                                5820
TAAATTTAAT AATTAAAGCA ACACACTCCG AAGAACTACC AGAAAATAGC ACTGTTGTAA
                                                                5880
ATTACAGAAA AACTATGCGC AGCGGTACTA TACACCCCAT TAAAAAAGAC ATATATATTT
                                                                5940
```

FIG. 7J

```
ATGACAACAA AAAATTTACT CTATACGATA GATACATATA TGGATACGAT AATAACTATG
                                                              6000
TTAATTTTTA TGAGGAGAAA AATGAAAAAG AGAAGGAATA CGAAGAAGAA GACGACAAGG
                                                              6060
CGTCTAGTTT ATGTGAAAAT AAAATTATAT TGTCGCAAAT TAACTGTGAA TCATTTGAAA
                                                              6120
ATGATTTTAA ATATTACCTC AGCGATTATA ACTACGCGTT TTCAATTATA GATAACACTA
                                                              6180
CAAATGTTCT TGTTGCGTTT GGTTGTATC GTTAATAAAA AACAAATTTA GCATTTATAA
                                                              6240
TTGTTTTATT ATTCAATAAT TACAAATAGG ATTGAGACCC TTGCAGTTGC CAGCAAACGG
                                                              6300
ACAGAGCTTG TCGAGGAGAG TTGTTGATTC ATTGTTTGCC TCCCTGCTGC GGTTTTTGAC
                                                              6360
CGAAGTTCAT GCCAGTCCAG CGTTTTGCA GCAGAAAAGC CGCCGACTTC GGTTTGCGGT
                                                              6420
CGGGAGTGAA GATCCCTTTC TTGTTACCGC CAACGCGCAA TATGCCTTGC GAGGTCGCAA
                                                              6480
AATCGGGCGAA ATTCCATACC TGTTCACCGA CGACGGCGCT GACGCGATCA AAGACGCGGT
                                                              6540
GATACATATC CAGCCATGCA CACTGATACT CTTCACTCCA CATGTCGGTG TACATTGAGT
                                                              6600
```

FIG. 7K

```
GCAGCCCGGC TAACGTATCC ACGCCGTATT CGGTGATGAT AATCGGCTGA TGCAGTTTCT
                                                                 6660
CCTGCCAGGC CAGAAGTTCT TTTTCCAGTA CCTTCTCTGC CGTTCCAAA TCGCCGCTT
                                                                 6720
GGACATACCA TCCGTAATAA CGGTTCAGGC ACAGCACATC AAAGAGATCG CTGATGGTAT
                                                                 6780
CGGTGTGAGC GTCGCAGAAC ATTACATTGA CGCAGGTGAT CGGACGCGTC GGGTCGAGTT
                                                                 6840
TACGCGTTGC TTCCGCCAGT GGCGCGAAAT ATTCCCGTGC ACCTTGCGGA CGGGTATCCG
                                                                 6900
GTTCGTTGGC AATACTCCAC ATCACCACGC TTGGGTGGTT TTTGTCACGC GCTATCAGCT
                                                                 6960
CTTTAATCGC CTGTAAGTGC GCTTGGTGAG TTTCCCCGTT GACTGCCTCT TCGTTGTACA
                                                                 7020
GTTCTTTCGG CTGTTGCCCC GCTTCGAAAC CAATGCCTAA AGAGAGGTTA AAGCCGACAG
                                                                 7080
CAGCAGTTTC ATCAATCACC ACGATGCCAT GTTCATCTGC CCAGTCGAGC ATCTCTTCAG
                                                                 7140
CGTAAGGGTA ATGCGAGGTA CGGTAGGAGT TGGCCCTAAT CCAGTCCATT AATGCCGTGGT
                                                                 7200
CGTGCACCAT CAGCACGTTA TCGAATCCTT TGCCACGCAA GTCCGCCATCT TCATGACGAC
                                                                 7260
```

FIG. 7L

```
CAAAGCCAGT AAAGTAGAAC GGTTTGTGGT TAATCAGGAA CTGTTCGCCC TTCACTGCCA
                                                                7320
CTGACCGGAT GCCGACGCGA AGCGGGTAGA TATCACACTC TGTCTGGCTT TTGGCTGTGA
                                                                7380
CGCACAGTTC ATAGAGATAA CCTTCACCCG GTTGCCAGAG GTGCGGATTC ACCACTTGCA
                                                                7440
AAGTCCCGCT AGTGCCTTGT CCAGTTGCAA CCACCTGTTG ATCCGCATCA CGCAGTTCAA
                                                                7500
CGCTGACATC ACCACCTGCC ACCACCTGCC AGTCAACAGA CGCGTGGTTA CAGTCTTGCG
                                                                7560
CGACATGCGT CACTACGGTG ATATCGTCCA CCCAGGTGTT CGGCGTGGTG TAGAGCATTA
                                                                7620
CGCTGCGATG GATTCCGGCA TAGTTAAAGA AATCATGGAA GTAAGATTGC TTTTTCTTGC
                                                                7680
CGTTTTCGTT GGTAATCACC ATTCCCGGGCG GGATAGTCTG CCAGTTCAGT TCGTTGTTCA
                                                                7740
CACAAACGGT GATACCCCTC GACGGATTAA AGACTTCAAG CGGTCAACTA TGAAGAAGTG
                                                                7800
TTCGTCTTCG TCCCAGTAAG CTATGTCTCT AGAATGTAGC CATCCATCCT TGTCAATCAA
                                                                7860
GGCGTTGGTC GCTTCCGGAT TGTTTACATA ACCGGACATA ATCATAGGTC CTCTGACACA
                                                                7920
```

FIG. 7M

```
TAATACGCCT CTCTGATTAA CGCCCAGCGT TTTCCCGGTA TCCAGATCCA CAACCTTCGC
                                                                7980
TTCAAAAAAT GGAACAACTT TACCGACCGC GCCCGGTTTA TCATCCCCCT CGGGTGTAAT
                                                                8040
CAGAATAGCT GATGTAGTCT CAGTGAGCCC ATATCCTTGT CGTATCCCTG GAAGATGGAA
                                                                8100
GCGTTTTGCA ACCGCTTCCC CGACTTCTTT CGAAAGAGGT GCGCCCCAG AAGCAATTTC
                                                                8160
GTGTAAATTA GATAAATCGT ATTTGTCAAT CAGAGTGCTT TTGGCGAAGA ATGAAAATAG
                                                                8220
GGTTGGTACT AGCAACGCAC TTTGAATTTT GTAATCCTGA AGGGATCGTA AAAACAGCTC
                                                                8280
TTCTTCAAAT CTATACATTA AGACGACTCG AAATCTACAT ATCAAATATC CGAGTGTAGT
                                                                8340
AAACATTCCA AAACCGTGAT GGAATGGAAC AACACTTAAA ATCGCAGTAT CCGGAATGAT
                                                                8400
TTGATTGCCA AAATAGGAT CTCTGGCATG CGAGAATCTA GCGCAGGCAG TTCTATGCGG
                                                                8460
AAGGGCCACA CCCTTAGGTA ACCCAGTAGA TCCAGAGGAA TTGTTTTGTC ACGATCAAAG
                                                                8520
GACTCTGGTA CAAAATCGTA TTCATTAAAA CCGGGAGGTA GATGAGATGT GACGAAGGTG
                                                                8580
```

FIG. 7N

```
TACATCGACT GAAATCCCTG GTAATCCGTT TTAGAATCCA TGATAATAAT TTTCTGGATT
                                                                8640
ATTGGTAATT TTTTTGCAC GTTCAAAATT TTTTGCAACC CCTTTTTGGA AACAAACACT
                                                                8700
ACGGTAGGCT GCGAAATGTT CATACTGTTG AGCAATTCAC GTTCATTATA AATGTCGTTC
                                                                8760
GCGGGCGCAA CTGCAACTCC GATAAATAAC GCGCCCAACA CCGGCATAAA GAATTGAAGA
                                                                8820
GAGTTTCAC TGCATACGAC GATTCTGTGA TTTGTATTCA GCCCATATCG TTTCATAGCT
                                                                8880
TCTGCCAACC GAACGGACAT TTCGAAGTAT TCCGCGTACG TGATGTTCAC CTCGATATGT
                                                                8940
GCATCTGTAA AAGGAATTGT TCCAGGAACC AGGGCGTATC TCTTCATAGC CTTATGCAGT
                                                                9000
TGCTCTCCAG CGGTTCCATT CTCTAGCTTT GCTTCTCAAT TTCTTATTTG CATAATGAGA
                                                                9060
AAAAAGGAA AATTAATTTT AACACCAATT CAGTAGTTGA TTGAGCAAAT GCGTTGCCAA
                                                                9120
AAAGGATGCT TTAGAGACAG TGTTCTCTGC ACAGATAAGG ACAAACATCA TTCAGAGGGA
                                                                9180
GTACCCAGAG CTGAGACTCC TAAGCCAGTG AGTGGCACAG CATTCTAGGG AGAAATATGC
                                                                9240
```

FIG. 7P

```
TTGTCATCAC CGAAGCCTGA TTCCGTAGAG CCACACCTTG GTAAGGGCCA ATCTGCTCAC   9300
ACAGGATAGA GAGGGCAGGA GCCAGGGCAG AGCATATAAG GTGAGGTAGG ATCAGTTGCT   9360
CCTCACATTT GCTTCTGACA TAGTTGTGTT GGGAGCTTGG ATCGATCCAC CATGGGCTTC   9420
AATACCCTGA TTGACTGGAA CAGCTGTAGC CCTGAACAGC AGCGTGCGCT GCTGACGCGT   9480
CCGGCGATTT CCGCCCTCTGA CAGTATTACC CGGACGGTCA GCGATATTCT GGATAATGCA   9540
AAAACGCGCG GTGACGATGC CCTGCGTGAA TACAGCGCTA AATTTGATAA AACAGAAGTG   9600
ACAGCGCTAC GCGTCACCCC TGAAGAGATC GCCGCCGCCG GCGCGGTCT GAGCGACGAA   9660
TTAAAACAGG CGATGACCGC TGCCGTCAAA AATATTGAAA CGTTCCATTC CGCGCAGACG   9720
CTACCGCTTG TAGATGTGGA AACCCAGCCA GGCGTGCCGT GCCAGCAGGT TACGCGTCCC   9780
GTCTCGTCTG TCGGTCTGTA TATTCCCGGC GGCTCGGCTC CGCTCTTCTC AACGGTGCTG   9840
ATGCTGGGCGA CGCCGGCGCG CGCCGGCGCG CATTGCGGGA TGCTAGAAGG TGGTTCTGTG CTCGCCGCCG   9900
```

FIG. 7Q

```
CCCATCGCTG ATGAAATCCT CTATGCGGGCG CAACTGTGTG GCGTGCAGGA ATTCTTTAAC   9960
CTCGGGCGCG CGCAGGGGAT TGCCGCTCTG GCCTTCGGCA GCGAGTCCGT ACCGAAAGTG  10020
GATAAAATTT TTGGCCCCGG CAACGCCTTT GTAACCGAAG CCAAACGTCA GGTCAGCCAG  10080
CGTCTCGACG GCGCGGCTAT CGATATGCCA GCCGAGCCGT CTGAAGTACT GGTGATCGCA  10140
GACAGCGGGCG CAACACCGGA TTTCGTCGCT GCTGACGCCT GATGCTGACA TTGCCCGCAA  10200
CCGGATTCCC AGGTGATCCT GCTGACGCCT GATGCTGACA TTGCCCGCAA GGTGGCGGAG  10260
GCGGTAGAAC GTCAACTGGC GGAACTGCCG CGGCGGGACA CCGGCCTGAGC GGCCCTGAGC  10320
GCCAGTCGTC TGATTGTGAC CAAAGATTTA GCGCAGTGCG TCGCCATCTC TAATCAGTAT  10380
GGGCCGGGAAC ACTTAATCAT CCAGACGCGC AATGCGCGCG ATTTGGTGGA TGCGATTACC  10440
AGCGCAGGCT CGGTATTTCT CGGCGACTGG TCGCCGGAAT CCGCCGGTGA TTACGCTTCC  10500
GGAACCAACC ATGTTTTACC GACCTATGGC CATACTGCTA CCTGTTCCAG CCTTGGGTTA  10560
```

FIG. 7R

```
GCGGATTTCC AGAAACGGAT GACCGTTCAG GAACTGTCGA AAGCGGGCTT TTCCGCTCTG
                                                                10620
GCATCAACCA TTGAAACATT GGCGGGGGCA GAACGTCTGA CCGCCCATAA AAATGCCGTG
                                                                10680
ACCCTGCGCG TAAACGCCCT CAAGGAGCAA GCATGAGCAC TGAAAACACT CTCAGCGTCG
                                                                10740
CTGACTTAGC CCGTGAAAAT GTCCGCAACC TGGAGATCCA GACATGATAA GATACATTGA
                                                                10800
TGAGTTTGGA CAAACCACAA CTAGAATGCA GTGAAAAAAA TGCTTTATTT GTGAAATTTG
                                                                10860
TGATGCTATT GCTTTATTTG TAACCATTAT AAGCTGCAAT AAACAAGTTA ACAACAACAA
                                                                10920
TTGCATTCAT TTTATGTTTC AGGTTCAGGG GGAGGTGTGG GAGGTTTTTT AAAGCAAGTA
                                                                10980
AAACCTCTAC AAATGTGGTA TGGCTGATTA TGATCTCTAG CTCGACGGGG CGCCTGGCCG
                                                                11040
CTACTAACTC TCTCCTCCCT CCTTTTTCCT GCAGGCTCAA GGCGCGGCATG CCCGACGGCG
                                                                11100
AGGATCTCGT CGTGACCCAT GGCGATGCCT GCTTGCCGAA TATCATGGTG GAAAATGGCC
                                                                11160
GCTTTTCTGG ATTCATCGAC TGTGGCCGGC TGGGTGTGGC GGACCGCTAT CAGGACATAG
                                                                11220
```

FIG. 7S

```
CGTGGCTAC CCGTGATATT GCTGAAGAGC TTGGCGGGCGA ATGGGCTGAC CGCTTCCTCG    11280
TGCTTTACGG TATCGCCGCT CCCGATTCGC AGCGGCATCGC CTTCTATCGC CTTCTTGACG   11340
AGTTCTTCTG AGCGGGACTC TGGGGTTCGA AATGACCGAC CAAGCGACGC CCAACCTGCC    11400
ATCACGAGAT TTCGATTCCA CCGCCGCCTT CTATGAAAGG TTGGGCTTCG GAATCGTTTT    11460
CCGGGACGCC GGCTGGATGA TCCTCCAGCG CGGGGATCTC ATGCTGGAGT TCTTCGCCCA    11520
CCCCAACTTG TTTATTGCAG CTTATAATGG TTACAAATAA AGCAATAGCA TCACAAATTT    11580
CACAAATAAA GCATTTTTT CACTGCATTC TAGTTGTGGT TTGTCCAAAC TCATCAATCT     11640
ATCTTATCAT GTCTGGATCG CGGCCCGGTCT CTCTCTAGCC CTAGGTCTAG ACTTGGCAGA   11700
ACATATCCAT CGGTCCGCC ATCTCCAGCA GCCGCACGCG GCGCATCTCG GGCAGCGTTG     11760
GGTCCTGGCC ACGGGTGCGC ATGATCGTGC TCCTGTCGTT GAGGACCCGG CTAGGCTGGC    11820
GGGGTTGCCT TACTGGTTAG CAGAATGAAT CACCGATACG CGAGCGAACG TGAAGCGACT    11880
```

FIG. 7T

```
GCTGCTGCAA AACGTCTGCG ACCTGAGCAA CAACATGAAT GGTCTTCGGT TTCCGTGTTT
                                                                11940
CGTAAAGTCT GGAAACGCGG AAGTCAGCGC CCTGCACCAT TATGTTCCGG ATCTGCATCG
                                                                12000
CAGGATGCTG CTGGCTACCC TGTGGAACAC CTACATCTGT ATTAACGAAG CGCTGGCATT
                                                                12060
GACCCTGAGT GATTTTCTC TGGTCCCGCC GCATCCATAC CGCCAGTTGT TAACCCTCAC
                                                                12120
AACGTTCCAG TAACCGGGCA TGTTCATCAT CAGTAACCCG TATCGTGAGC ATCCTCTCTC
                                                                12180
GTTTCATCGG TATCATTACC CCCATGAACA GAAATCCCCC TTACACGGAG GCATCAGTGA
                                                                12240
CCAAACAGGA AAAAACCGCC CTTAACATGG CCCGCTTTAT CAGAAGCCAG ACATTAACGC
                                                                12300
TTCTGGGAGAA ACTCAACGAG CTGGACGCGG ATGAACAGGC AGACATCTGT GAATCGCTTC
                                                                12360
ACGACCACGC TGATGAGCTT TACCGCAGCT GCCTCGCGCG TTTCGGTGAT GACGGTGAAA
                                                                12420
ACCTCTGACA CATGCAGCTC CCGGAGACGG TCACAGCTTG TCTGTAAGCG GATGCCGGGA
                                                                12480
GCAGACAAGC CCGTCAGGGC GCGTCAGCGG GTGTTGGCGG GTGTCGGGGC GCAGCCATGA
                                                                12540
```

FIG. 7U

```
CCCAGTCACG TAGCGATAGC GGAGTGTATA CTGGCTTAAC TATGCGGGCAT CAGAGCAGAT   12600
TGTACTGAGA GTGCACCATA TGCGGTGTGA AATACCGCAC AGATGCGTAA GGAGAAATA    12660
CCGCATCAGG CGCTCTTCCG CTTCCTCGCT CACTGACTCG CTGCGCTCGG TCGTTCGGCT   12720
GCGGCGAGCG GTATCAGCTC ACTCAAAGGC GGTAATACGG TTATCCACAG AATCAGGGGA   12780
TAACGCAGGA AAGAACATGT GAGCAAAAGG CCAGCAAAAG GCCAGGAACC GTAAAAAGGC   12840
CGCGTTGCTG GCGTTTTTCC ATAGGCTCCG CCCCCCTGAC GAGCATCACA AAAATCGACG   12900
CTCAAGTCAG AGGTGGGCGAA ACCCGACAGG ACTATAAAGA TACCAGGCGT TTCCCCCTGG   12960
AAGCTCCCTC GTGCGCTCTC CTGTTCCGAC CCTGCCGCTT ACCGGATACC TGTCCGCCTT   13020
TCTCCCTTCG GGAAGCGTGG CGCTTTCTCA TAGCTCACGC TGTAGGTATC TCAGTTCGGT   13080
GTAGGTCGTT CGCTCCAAGC TGGGCTGTGT GCACGAACCC CCGTTCAGC CCGACCGCTG    13140
CGCCTTATCC GGTAACTATC GTCTTGAGTC CAACCCGGTA AGACACGACT TATCGCCACT   13200
```

FIG. 7V

```
GGCAGCAGCC ACTGGTAACA GGATTAGCAG AGGCAGGTAT GTAGGCGGTG CTACAGAGTT   13260
CTTGAAGTGG TGGCCTAACT ACGGCTACAC TAGAAGGACA GTATTTGGTA TCTGCGCTCT   13320
GCTGAAGCCA GTTACCTTCG GAAAAAGAGT TGGTAGCTCT TGATCCGGCA AACAAACCAC   13380
CGCTGGGTAGC GGTGGTTTTT TTGTTTGCAA GCAGCAGATT ACGCGCAGAA AAAAAGGATC   13440
TCAAGAAGAT CCTTTGATCT TTTCTACGGG GTCTGACGCT CAGTGGAACG AAAACTCACG   13500
TTAAGGGATT TTGGTCATGA GATTATCAAA AAGGATCTTC ACCTAGATCC TTTTAAATTA   13560
AAAATGAAGT TTTAAATCAA TCTAAAGTAT ATATGAGTAA ACTTGGTCTG ACAGTTACCA   13620
ATGCTTAATC AGTGAGGCAC CTATCTCAGC GATCTGTCTA TTTCGTTCAT CCATAGTTGC   13680
CTGACTCCCC GTCGTGTAGA TAACTACGAT ACGGGAGGGC TTACCATCTG GCCCCAGTGC   13740
TGCAATGATA CCGCGAGACC CACGCTCACC GGCTCCAGAT TTATCAGCAA TAAACCAGCC   13800
AGCCGGAAGG GCCGAGCGCA GAAGTGGTCC TGCAACTTTA TCCGCCTCCA TCCAGTCTAT   13860
```

FIG. 7W

```
TAATTGTTGC CGGGAAGCTA GAGTAAGTAG TTCGCCAGTT AATAGTTTGC GCAACGTTGT   13920
TGCCATTGCT GCAGGCATCG TGGTGTCACG CTCGTCGTTT GGTATGGCTT CATTCAGCTC   13980
CGGTTCCCAA CGATCAAGGC GAGTTACATG ATCCCCCATG TTGTGCAAAA AAGCGGTTAG   14040
CTCCTTCGGT CCTCCGATCG TTGTCAGAAG TAAGTTGGCC GCAGTGTTAT CACTCATGGT   14100
TATGGCAGCA CTGCATAATT CTCTTACTGT CATGCCATCC GTAAGATGCT TTTCTGTGAC   14160
TGGTGAGTAC TCAACCAAGT CATTCTGAGA ATAGTGTATG CGGCGACCGA GTTGCTCTTG   14220
CCCGGCGTCA ACACGGGATA ATACCGCGCC ACATAGCAGA ACTTTAAAAG TGCTCATCAT   14280
TGGAAAACGT TCTTCGGGGC GAAAACTCTC AAGGATCTTA CCGCTGTTGA GATCCAGTTC   14340
GATGTAACCC ACTCGTGCAC CCAACTGATC TTCAGCATCT TTTACTTTCA CCAGCGTTTC   14400
TGGGTGAGCA AAAACAGGAA GGCAAAATGC CGCAAAAAAG GGAATAAGGG CGACACGGAA   14460
ATGTTGAATA CTCATACTCT TCCTTTTTCA ATATTATTGA AGCATTTATC AGGGTTATTG   14520
```

FIG. 7X

```
TCTCATGAGC GGATACATAT TTGAATGTAT TTAGAAAAAT AAACAAATAG GGGTTCCGCG
                                                              14580
CACATTTCCC CGAAAAGTGC CACCTGACGT CTAAGAAACC ATTATTATCA TGACATTAAC
                                                              14640
CTATAAAAAT AGGCGTATCA CGAGGCCCTT TCGTCTTCAA GAA
                                              14683
```

METHOD FOR INTEGRATING GENES AT SPECIFIC SITES IN MAMMALIAN CELLS VIA HOMOLOGOUS RECOMBINATION AND VECTORS FOR ACCOMPLISHING THE SAME

RELATED APPLICATIONS

This application is a continuation-in-part of U.S. Ser. No. 08/819,866, U.S. Pat. No. 5,830,698, filed on Mar. 14, 1997.

FIELD OF THE INVENTION

The present invention relates to a process of targeting the integration of a desired exogenous DNA to a specific location within the genome of a mammalian cell. More specifically, the invention describes a novel method for identifying a transcriptionally active target site ("hot spot") in the mammalian genome, and inserting a desired DNA at this site via homologous recombination. The invention also optionally provides the ability for gene amplification of the desired DNA at this location by co-integrating an amplifiable selectable marker, e.g., DHFR, in combination with the exogenous DNA. The invention additionally describes the construction of novel vectors suitable for accomplishing the above, and further provides mammalian cell lines produced by such methods which contain a desired exogenous DNA integrated at a target hot spot.

BACKGROUND

Technology for expressing recombinant proteins in both prokaryotic and eukaryotic organisms is well established. Mammalian cells offer significant advantages over bacteria or yeast for protein production, resulting from their ability to correctly assemble, glycosylate and post-translationally modify recombinantly expressed proteins. After transfection into the host cells, recombinant expression constructs can be maintained as extrachromosomal elements, or may be integrated into the host cell genome. Generation of stably transfected mammalian cell lines usually involves the latter; a DNA construct encoding a gene of interest along with a drug resistance gene (dominant selectable marker) is introduced into the host cell, and subsequent growth in the presence of the drug allows for the selection of cells that have successfully integrated the exogenous DNA. In many instances, the gene of interest is linked to a drug resistant selectable marker which can later be subjected to gene amplification. The gene encoding dihydrofolate reductase (DHFR) is most commonly used for this purpose. Growth of cells in the presence of methotrexate, a competitive inhibitor of DHFR, leads to increased DHFR production by means of amplification of the DHFR gene. As flanking regions of DNA will also become amplified, the resultant coamplification of a DHFR linked gene in the transfected cell line can lead to increased protein production, thereby resulting in high level expression of the gene of interest.

While this approach has proven successful, there are a number of problems with the system because of the random nature of the integration event. These problems exist because expression levels are greatly influenced by the effects of the local genetic environment at the gene locus, a phenomena well documented in the literature and generally referred to as "position effects" (for example, see Al-Shawi et al, *Mol. Cell. Biol.*, 10:1192–1198 (1990); Yoshimura et al, *Mol. Cell. Biol.*, 7:1296–1299 (1987)). As the vast majority of mammalian DNA is in a transcriptionally inactive state, random integration methods offer no control over the transcriptional fate of the integrated DNA. Consequently, wide variations in the expression level of integrated genes can occur, depending on the site of integration. For example, integration of exogenous DNA into inactive, or transcriptionally "silent" regions of the genome will result in little or no expression. By contrast integration into a transcriptionally active site may result in high expression.

Therefore, when the goal of the work is to obtain a high level of gene expression, as is typically the desired outcome of genetic engineering methods, it is generally necessary to screen large numbers of transfectants to find such a high producing clone. Additionally, random integration of exogenous DNA into the genome can in some instances disrupt important cellular genes, resulting in an altered phenotype. These factors can make the generation of high expressing stable mammalian cell lines a complicated and laborious process.

Recently, our laboratory has described the use of DNA vectors containing translationally impaired dominant selectable markers in mammalian gene expression. (This is disclosed in U.S. Pat. No. 5,648,267).

These vectors contain a translationally impaired neomycin phosphotransferase (neo) gene as the dominant selectable marker, artificially engineered to contain an intron into which a DHFR gene along with a gene or genes of interest is inserted. Use of these vectors as expression constructs has been found to significantly reduce the total number of drug resistant colonies produced, thereby facilitating the screening procedure in relation to conventional mammalian expression vectors. Furthermore, a significant percentage of the clones obtained using this system are high expressing clones. These results are apparently attributable to the modifications made to the neo selectable marker. Due to the translational impairment of the neo gene, transfected cells will not produce enough neo protein to survive drug selection, thereby decreasing the overall number of drug resistant colonies. Additionally, a higher percentage of the surviving clones will contain the expression vector integrated into sites in the genome where basal transcription levels are high, resulting in overproduction of neo, thereby allowing the cells to overcome the impairment of the neo gene. Concomitantly, the genes of interest linked to neo will be subject to similar elevated levels of transcription. This same advantage is also true as a result of the artificial intron created within neo; survival is dependent on the synthesis of a functional neo gene, which is in turn dependent on correct and efficient splicing of the neo introns. Moreover, these criteria are more likely to be met if the vector DNA has integrated into a region which is already highly transcriptionally active.

Following integration of the vector into a transcriptionally active region, gene amplification is performed by selection for the DHFR gene. Using this system, it has been possible to obtain clones selected using low levels of methotrexate (50 nM), containing few (<10) copies of the vector which secrete high levels of protein (>55 pg/cell/day). Furthermore, this can be achieved in a relatively short period of time. However, the success in amplification is variable. Some transcriptionally active sites cannot be amplified and therefore the frequency and extent of amplification from a particular site is not predictable.

Overall, the use of these translationally impaired vectors represents a significant improvement over other methods of random integration. However, as discussed, the problem of lack of control over the integration site remains a significant concern.

One approach to overcome the problems of random integration is by means of gene targeting, whereby the exogenous DNA is directed to a specific locus within the host genome. The exogenous DNA is inserted by means of homologous recombination occurring between sequences of DNA in the expression vector and the corresponding homologous sequence in the genome. However, while this type of recombination occurs at a high frequency naturally in yeast and other fungal organisms, in higher eukaryotic organisms it is an extremely rare event. In mammalian cells, the frequency of homologous versus non-homologous (random integration) recombination is reported to range from 1/100 to 1/5000 (for example, see Capecchi, *Science*, 244:1288–1292 (1989); Morrow and Kucherlapati, *Curr. Op. Biotech.*, 4:577–582 (1993)).

One of the earliest reports describing homologous recombination in mammalian cells comprised an artificial system created in mouse fibroblasts (Thomas et al, *Cell*, 44:419–428 (1986)). A cell line containing a mutated, non-functional version of the neo gene integrated into the host genome was created, and subsequently targeted with a second non-functional copy of neo containing a different mutation. Reconstruction of a functional neo gene could occur only by gene targeting. Homologous recombinants were identified by selecting for G418 resistant cells, and confirmed by analysis of genomic DNA isolated from the resistant clones.

Recently, the use of homologous recombination to replace the heavy and light immunoglobulin genes at endogenous loci in antibody secreting cells has been reported. (U.S. Pat. No. 5,202,238, Fell et al, (1993).) However, this particular approach is not widely applicable, because it is limited to the production of immunoglobulins in cells which endogenously express immunoglobulins, e.g., B cells and myeloma cells. Also, expression is limited to single copy gene levels because co-amplification after homologous recombination is not included. The method is further complicated by the fact that two separate integration events are required to produce a functional immunoglobulin: one for the light chain gene followed by one for the heavy chain gene.

An additional example of this type of system has been reported in NS/0 cells, where recombinant immunoglobulins are expressed by homologous recombination into the immunoglobulin gamma 2A locus (Hollis et al, international patent application # PCT/IB95 (00014).) Expression levels obtained from this site were extremely high—on the order of 20 pg/cell/day from a single copy integrant. However, as in the above example, expression is limited to this level because an amplifiable gene is not contegrated in this system. Also, other researchers have reported aberrant glycosylation of recombinant proteins expressed in NS/0 cells (for example, see Flesher et al, *Biotech. and Bioeng.*, 48:399–407 (1995)), thereby limiting the applicability of this approach.

The cre-loxP recombination system from bacteriophage P1 has recently been adapted and used as a means of gene targeting in eukaryotic cells. Specifically, the site specific integration of exogenous DNA into the Chinese hamster ovary (CHO) cell genome sing cre recombinase and a series of lox containing vectors have been described. (Fukushige and Sauer, *Proc. Natl. Acad. Sci. USA*, 89:7905–7909 (1992).) This system is attractive in that it provides for reproducible expression at the same chromosomal location. However, no effort was made to identify a chromosomal site from which gene expression is optimal, and as in the above example, expression is limited to single copy levels in this system. Also, it is complicated by the fact that one needs to provide for expression of a functional recombinase enzyme in the mammalian cell.

The use of homologous recombination between an introduced DNA sequence and its endogenous chromosomal locus has also been reported to provide a useful means of genetic manipulation in mammalian cells, as well as in yeast cells. (See e.g., Bradley et al, *Meth. Enzymol.*, 223:855–879 (1993); Capecchi, *Science*, 244:1288–1292 (1989); Rothstein et al, *Meth. Enzymol.*, 194:281–301 (1991)). To date, most mammalian gene targeting studies have been directed toward gene disruption ("knockout") or site-specific mutagenesis of selected target gene loci in mouse embryonic stem (ES) cells. The creation of these "knockout" mouse models has enabled scientists to examine specific structure-function issues and examine the biological importance of a myriad of mouse genes. This field of research also has important implications in terms of potential gene therapy applications.

Also, vectors have recently been reported by Cell-tech (Kent, U.K.) which purportedly are targeted to transcriptionally active sites in NSO cells, which do not require gene amplification (Peakman et al, *Hum. Antibod. Hybridomas*, 5:65–74 (1994)). However, levels of immunoglobulin secretion in these unamplified cells have not been reported to exceed 20 pg/cell/day, while in amplified CHO cells, levels as high as 100 pg/cell/day can be obtained (Id.).

It would be highly desirable to develop a gene targeting system which reproducibly provided for the integration of exogenous DNA into a predetermined site in the genome known to be transcriptionally active. Also, it would be desirable if such a gene targeting system would further facilitate co-amplification of the inserted DNA after integration. The design of such a system would allow for the reproducible and high level expression of any cloned gene of interest in a mammalian cell, and undoubtedly would be of significant interest to many researchers.

In this application, we provide a novel mammalian expression system, based on homologous recombination occurring between two artificial substrates contained in two different vectors. Specifically, this system uses a combination of two novel mammalian expression vectors, referred to as a "marking" vector and a "targeting" vector.

Essentially, the marking vector enables the identification and marking of a site in the mammalian genome which is transcriptionally active, i.e., a site at which gene expression levels are high. This site can be regarded as a "hot spot" in the genome. After integration of the marking vector, the subject expression system enables another DNA to be integrated at this site, i.e., the targeting vector, by means of homologous recombination occurring between DNA sequences common to both vectors. This system affords significant advantages over other homologous recombination systems.

Unlike most other homologous systems employed in mammalian cells, this system exhibits no background. Therefore, cells which have only undergone random integration of the vector do not survive the selection. Thus, any gene of interest cloned into the targeting plasmid is expressed at high levels from the marked hot spot. Accordingly, the subject method of gene expression substantially or completely eliminates the problems inherent to systems of random integration, discussed in detail above. Moreover, this system provides reproducible and high level expression of any recombinant protein at the same transcriptionally active site in the mammalian genome. In addition, gene amplification may be effected at this particular transcriptionally active site by including an amplifiable dominant selectable marker (e.g. DHFR) as part of the marking vector.

Objects of the Invention

Thus, it is an object of the invention to provide an improved method for targeting a desired DNA to a specific site in a mammalian cell.

It is a more specific object of the invention to provide a novel method for targeting a desired DNA to a specific site in a mammalian cell via homologous recombination.

It is another specific object of the invention to provide novel vectors for achieving site specific integration of a desired DNA in a mammalian cell.

It is still another object of the invention to provide novel mammalian cell lines which contain a desired DNA integrated at a predetermined site which provides for high expression.

It is a more specific object of the invention to provide a novel method for achieving site specific integration of a desired DNA in a Chinese hamster ovary (CHO) cell.

It is another more specific object of the invention to provide a novel method for integrating immunoglobulin genes, or any other genes, in mammalian cells at predetermined chromosomal sites that provide for high expression.

It is another specific object of the invention to provide novel vectors and vector combinations suitable for integrating immunoglobulin genes into mammalian cells at predetermined sites that provide for high expression.

It is another object of the invention to provide mammalian cell lines which contain immunoglobulin genes integrated at predetermined sites that provide for high expression.

It is an even more specific object of the invention to provide a novel method for integrating immunoglobulin genes into CHO cells that provide for high expression, as well as novel vectors and vector combinations that provide for such integration of immunoglobulin genes into CHO cells.

In addition, it is a specific object of the invention to provide novel CHO cell lines which contain immunoglobulin genes integrated at predetermined sites that provide for high expression, and have been amplified by methotrexate selection to secrete even greater amounts of functional immunoglobulins.

BRIEF DESCRIPTION OF THE FIGURES

FIG. 2(a) shows a map of a targeting plasmid referred to "Molly". Molly is shown here encoding the anti-CD20 immunoglobulin genes, expression of which is described in Example 1.

FIG. 7 contains a map of the targeting plasmid, "Mandy," shown here encoding anti-CD23 genes, the expression of which is disclosed in Example 5.

DETAILED DESCRIPTION OF THE INVENTION

Figure 1A:
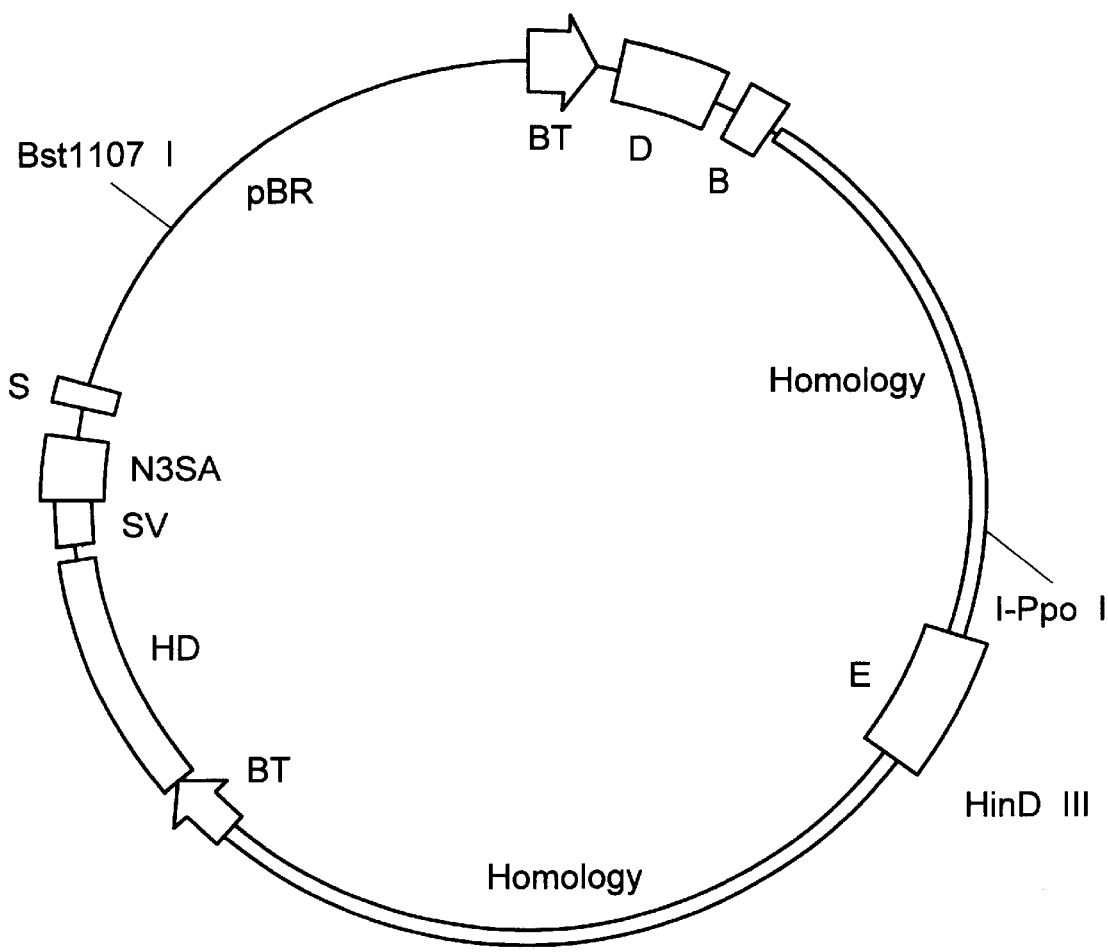
FIGS. 1A–1B depict a map of a marking plasmid according to the invention referred to as Desmond. The plasmid is shown in circular form (1a) as well as a linearized version used for transfection (1b).

The invention provides a novel method for integrating a desired exogenous DNA at a target site within the genome of a mammalian cell via homologous recombination. Also, the invention provides novel vectors for achieving the site specific integration of a DNA at a target site in the genome of a mammalian cell.

More specifically, the subject cloning method provides for site specific integration of a desired DNA in a mammalian cell by transfection of such cell with a "marker plasmid" which contains a unique sequence that is foreign to the mammalian cell genome and which provides a substrate for homologous recombination, followed by transfection with a "target plasmid" containing a sequence which provides for homologous recombination with the unique sequence contained in the marker plasmid, and further comprising a desired DNA that is to be integrated into the mammalian cell. Typically, the integrated DNA will encode a protein of interest, such as an immunoglobulin or other secreted mammalian glycoprotein.

The exemplified homologous recombination system uses the neomycin phosphotransferase gene as a dominant selectable marker. This particular marker was utilized based on the following previously published observations;

(i) the demonstrated ability to target and restore function to a mutated version of the neo gene (cited earlier) and (ii) our development of translationally impaired expression vectors, in which the neo gene has been artificially created as two exons with a gene of interest inserted in the intervening intron; neo exons are correctly spliced and translated in vivo, producing a functional protein and thereby conferring G418 resistance on the resultant cell population. In this application, the neo gene is split into three exons. The third exon of neo is present on the "marker" plasmid and becomes integrated into the host cell genome upon integration of the marker plasmid into the mammalian cells. Exons 1 and 2 are present on the targeting plasmid, and are separated by an intervening intron into which at least one gene of interest is cloned. Homologous recombination of the targeting vector with the integrated marking vector results in correct splicing of all three exons of the neo gene and thereby expression of a functional neo protein (as determined by selection for G418 resistant colonies). Prior to designing the current expression system, we had experimentally tested the functionality of such a triply spliced neo construct in mammalian cells. The results of this control experiment indicated that all three neo exons were properly spliced and therefore suggested the feasibility of the subject invention.

However, while the present invention is exemplified using the neo gene, and more specifically a triple split neo gene, the general methodology should be efficacious with other dominant selectable markers.

As discussed in greater detail infra, the present invention affords numerous advantages to conventional gene expression methods, including both random integration and gene targeting methods. Specifically, the subject invention provides a method which reproducibly allows for site-specific integration or a desired DNA into a transcriptionally active domain of a mammalian cell. Moreover, because the subject method introduces an artificial region of "homology" which acts as a unique substrate for homologous recombination and the insertion of a desired DNA, the efficacy of subject invention does not require that the cell endogenously contain or express a specific DNA. Thus, the method is generically applicable to all mammalian cells, and can be used to express any type of recombinant protein.

The use of a triply spliced selectable marker, e.g., the exemplified triply spliced neo construct, guarantees that all G418 resistant colonies produced will arise from a homologous recombination event (random integrants will not produce a functional neo gene and consequently will not survive G418 selection). Thus, the subject invention makes it easy to screen for the desired homologous event. Furthermore, the frequency of additional random integrations in a cell that has undergone a homologous recombination event appears to be low.

Based on the foregoing, it is apparent that a significant advantage of the invention is that it substantially reduces the number of colonies that need be screened to identify high producer clones, i.e., cell lines containing a desired DNA which secrete the corresponding protein at high levels. On average, clones containing integrated desired DNA may be identified by screening about 5 to 20 colonies (compared to several thousand which must be screened when using standard random integration techniques, or several hundred using the previously described intronic insertion vectors) Additionally, as the site of integration was preselected and comprises a transcriptionally active domain, all exogenous DNA expressed at this site should produce comparable, i.e. high levels of the protein of interest.

Moreover, the subject invention is further advantageous in that it enables an amplifiable gene to be inserted on integration of the marking vector. Thus, when a desired gene is targeted to this site via homologous recombination, the subject invention allows for expression of the gene to be further enhanced by gene amplification. In this regard, it has been reported in from the literature that different genomic sites have different capacities for gene amplification (Meinkoth et al, *Mol. Cell Biol.*, 7:1415–1424 (1987)). Therefore, this technique is further advantageous as it allows for the placement of a desired gene of interest at a specific site that is both transcriptionally active and easily amplified. Therefore, this should significantly reduce the amount of time required to isolate such high producers.

Specifically, while conventional methods for the construction of high expressing mammalian cell lines can take 6 to 9 months, the present invention allows for such clones to be isolated on average after only about 3–6 months. This is due to the fact that conventionally isolated clones typically must be subjected to at least three rounds of drug resistant gene amplification in order to reach satisfactory levels of gene expression. As the homologously produced clones are generated from a preselected site which is a high expression site, fewer rounds of amplification should be required before reaching a satisfactory level of production.

Still further, the subject invention enables the reproducible selection of high producer clones wherein the vector is integrated at low copy number, typically single copy. This is advantageous as it enhances the stability of the clones and avoids other potential adverse side-effects associated with high copy number. As described supra, the subject homologous recombination system uses the combination of a "marker plasmid" and a "targeting plasmid" which are described in more detail below.

The "marker plasmid" which is used to mark and identify a transcriptionally hot spot will comprise at least the following sequences:

(i) a region of DNA that is heterologous or unique to the genome of the mammalian cell, which functions as a source of homology, allows for homologous recombination (with a DNA contained in a second target plasmid). More specifically, the unique region of DNA (i) will generally comprise a bacterial, viral, yeast synthetic, or other DNA which is not normally present in the mammalian cell genome and which further does not comprise significant homology or sequence identity to DNA contained in the genome of the mammalian cell. Essentially, this sequence should be sufficiently different to mammalian DNA that it will not significantly recombine with the host cell genome via homologous recombination. The size of such unique DNA will generally be at least about 2 to 10 kilobases in size, or higher, more preferably at least about 10 kb, as several other investigators have noted an increased frequency of targeted recombination as the size of the homology region is increased (Capecchi, *Science*, 244:1288–1292 (1989)).

The upper size limit of the unique DNA which acts as a site for homologous recombination with a sequence in the second target vector is largely dictated by potential stability constraints (if DNA is too large it may not be easily integrated into a chromosome and the difficulties in working with very large DNAs.

(ii) a DNA including a fragment of a selectable marker DNA, typically an exon of a dominant selectable marker gene. The only essential feature of this DNA is that it not encode a functional selectable marker protein unless it is expressed in association with a sequence contained in the target plasmid. Typically, the target plasmid will comprise the remaining exons of the dominant selectable marker gene (those not comprised in "targeting" plasmid). Essentially, a functional selectable marker should only be produced if homologous recombination occurs (resulting in the association and expression of this marker DNA (i) sequence together with the portion(s) of the selectable marker DNA fragment which is (are) contained in the target plasmid).

As noted, the current invention exemplifies the use of the neomycin phosphotransferase gene as the dominant selectable marker which is "split" in the two vectors. However, other selectable markers should also be suitable, e.g., the Salmonella histidinol dehydrogenase gene, hygromycin phosphotransferase gene, herpes simplex virus thymidine kinase gene, adenosine deaminase gene, glutamine synthetase gene and hypoxanthine-guanine phosphoribosyl transferase gene.

(iii) a DNA which encodes a functional selectable marker protein, which selectable marker is different from the selectable marker DNA (ii). This selectable marker provides for the successful selection of mammalian cells wherein the marker plasmid is successfully integrated into the cellular DNA. More preferably, it is desirable that the marker plasmid comprise two such dominant selectable marker DNAs, situated at opposite ends of the vector. This is advantageous as it enables integrants to be selected using different selection agents and further enables cells which contain the entire vector to be selected. Additionally, one marker can be an amplifiable marker to facilitate gene amplification as discussed previously. Any of the dominant selectable marker listed in (ii) can be used as well as others generally known in the art.

Moreover, the marker plasmid may optionally further comprise a rare endonuclease restriction site. This is potentially desirable as this may facilitate cleavage. If present, such rare restriction site should be situated close to the middle of the unique region that acts as a substrate for homologous recombination. Preferably such sequence will be at least about 12 nucleotides. The introduction of a double stranded break by similar methodology has been reported to enhance the frequency of homologous recombination. (Choulika et al, *Mol. Cell. Biol.*, 15:1968–1973 (1995)). However, the presence of such sequence is not essential.

The "targeting plasmid" will comprise at least the following sequences:

(1) the same unique region of DNA contained in the marker plasmid or one having sufficient homology or sequence identity therewith that said DNA is capable of combining via homologous recombination with the unique region (i) in the marker plasmid. Suitable types of DNAs are described supra in the description of the unique region of DNA (1) in the marker plasmid.

(2) The remaining exons of the dominant selectable marker, one exon of which is included as (ii) in the marker plasmid listed above. The essential features of this DNA fragment is that it result in a functional (selectable) marker protein only if the target plasmid integrates via homologous recombination (wherein such recombination results in the association of this DNA with the other fragment of the selectable marker DNA contained in the marker plasmid) and further that it allow for insertion of a desired exogenous DNA. Typically, this DNA will comprise the remaining exons of the selectable marker DNA which are separated by an intron. For example, this DNA may comprise the first two exons of the neo gene and the marker plasmid may comprise the third exon (back third of neo).

(3) The target plasmid will also comprise a desired DNA, e.g., one encoding a desired polypeptide, preferably inserted within the selectable marker DNA fragment contained in the plasmid. Typically, the DNA will be inserted in an intron which is comprised between the exons of the selectable marker DNA. This ensures that the desired DNA is also integrated if homologous recombination of the target plasmid and the marker plasmid occurs. This intron may be naturally occurring or it may be engineered into the dominant selectable marker DNA fragment.

This DNA will encode any desired protein, preferably one having pharmaceutical or other desirable properties. Most typically the DNA will encode a mammalian protein, and in the current examples provided, an immunoglobulin or an immunoadhesin. However the invention is not in any way limited to the production of immunoglobulins.

As discussed previously, the subject cloning method is suitable for any mammalian cell as it does not require for efficacy that any specific mammalian sequence or sequences be present. In general, such mammalian cells will comprise those typically used for protein expression, e.g., CHO cells, myeloma cells, COS cells, BHK cells, Sp2/0 cells, NIH 3T3 and HeLa cells. In the examples which follow, CHO cells were utilized. The advantages thereof include the availability of suitable growth medium, their ability to grow efficiently and to high density in culture, and their ability to express mammalian proteins such as immunoglobulins in biologically active form.

Further, CHO cells were selected in large part because of previous usage of such cells by the inventors for the expression of immunoglobulins (using the translationally impaired dominant selectable marker containing vectors described previously). Thus, the present laboratory has considerable experience in using such cells for expression. However, based on the examples which follow, it is reasonable to expect similar results will be obtained with other mammalian cells.

In general, transformation or transfection of mammalian cells according to the subject invention will be effected according to conventional methods. So that the invention may be better understood, the construction of exemplary vectors and their usage in producing integrants is described in the examples below.

EXAMPLE 1

Design and Preparation of Marker and Targeting Plasmid DNA Vectors

The marker plasmid herein referred to as "Desmond" was assembled from the following DNA elements:

(a) Murine dihydrofolate reductase gene (DHFR), incorporated into a transcription cassette, comprising the mouse beta globin promoter 5" to the DHFR start site, and bovine growth hormone poly adenylation signal 3" to the stop codon. The DHFR transcriptional cassette was isolated from TCAE6, an expression vector created previously in this laboratory (Newman et al, 1992, *Bio-technology*, 10:1455–1460).

(b) *E. coli* β-galactosidase gene—commercially available, obtained from Promega as pSV-b-galactosidase control vector, catalog # E1081.

(c) Baculovirus DNA, commercially available, purchased from Clontech as pBAKPAK8, cat # 6145-1.

(d) Cassette comprising promoter and enhancer elements from Cytomegalovirus and SV40 virus. The cassette was generated by PCR using a derivative of expression vector TCAE8 (Reff et al, *Blood*, 83:435–445 (1994)). The enhancer cassette was inserted within the baculovirus sequence, which was first modified by the insertion of a multiple cloning site.

(e) *E. coli* GUS (glucuronidase) gene, commercially available, purchased from Clontech as pB101, cat. # 6017-1.

(f) Firefly luciferase gene, commercially available, obtained from Promega as pGEM-Luc (catalog # E1541).

(g) *S. typhimurium* histidinol dehydrogenase gene (HisD). This gene was originally a gift from (Donahue et al, *Gene*, 18:47–59 (1982)), and has subsequently been incorporated into a transcription cassette comprising the mouse beta globin major promoter 5' to the gene, and the SV40 polyadenylation signal 3' to the gene.

The DNA elements described in (a)–(g) were combined into a pBR derived plasmid backbone to produce a 7.7 kb contiguous stretch of DNA referred to in the attached figures as "homology". Homology in this sense refers to sequences of DNA which are not part of the mammalian genome and are used to promote homologous recombination between transfected plasmids sharing the same homology DNA sequences.

(h) Neomycin phosphotransferase gene from TN5 (Davis and Smith, *Ann. Rev. Micro.*, 32:469–518 (1978)). The complete neo gene was subcloned into pBluescript SK- (Stratagene catalog # 212205) to facilitate genetic manipulation. A synthetic linker was then inserted into a unique Pst1 site occurring across the codons for amino acid 51 and 52 of neo. This linker encoded the necessary DNA elements to create an artificial splice donor site, intervening intron and splice acceptor site within the neo gene, thus creating two separate exons, presently referred to as neo exon 1 and 2. Neo exon 1 encodes the first 51 amino acids of neo, while exon 2 encodes the remaining 203 amino acids plus the stop codon of the protein A Not1 cloning site was also created within the intron.

Neo exon 2 was further subdivided to produce neo exons 2 and 3. This was achieved as follows: A set of PCR primers were designed to amplify a region of DNA encoding neo exon 1, intron and the first 111 ⅔ amino acids of exon2. The 3' PCR primer resulted in the introduction of a new 5' splice site immediately after the second nucleotide of the codon for amino acid 111 in exon 2, therefore generating a new smaller exon 2. The DNA fragment now encoding the original exon 1, intron and new exon 2 was then subcloned and propagated in a pBR based vector. The remainder of the original exon 2 was used as a template for another round of PCR amplification, which generated "exon3". The 5' primer for this round of amplification introduced a new splice acceptor site at the 5' side of the newly created exon 3, i.e. before the final nucleotide of the codon for amino acid 111. The resultant 3 exons of neo encode the following information: exon 1—the first 51 amino acids of neo; exon 2—the next 111 ⅔ amino acids, and exon 3 the final 91 ⅓ amino acids plus the translational stop codon of the neo gene.

Neo exon 3 was incorporated along with the above mentioned DNA elements into the marking plasmid "Desmond". Neo exons 1 and 2 were incorporated into the targeting plasmid "Molly". The Not1 cloning site created within the intron between exons 1 and 2 was used in subsequent cloning steps to insert genes of interest into the targeting plasmid.

A second targeting plasmid "Mandy" was also generated. This plasmid is almost identical to "Molly" (some restriction sites on the vector have been changed) except that the original HisD and DHFR genes contained in "Molly" were inactivated. These changes were incorporated because the Desmond cell line was no longer being cultured in the presence of Histidinol, therefore it seemed unnecessary to include a second copy of the HisD gene. Additionally, the DHFR gene was inactivated to ensure that only a single DHFR gene, namely the one present in the Desmond marked site, would be amplifiable in any resulting cell lines. "Mandy" was derived from "Molly" by the following modifications:

(i) A synthetic linker was inserted in the middle of the DHFR coding region. This linker created a stop codon and shifted the remainder of the DHFR coding region out of frame, therefore rendering the gene nonfunctional.

(ii) A portion of the HisD gene was deleted and replaced with a PCR generated HisD fragment lacking the promoter and start codon of the gene.

Figure 1B:
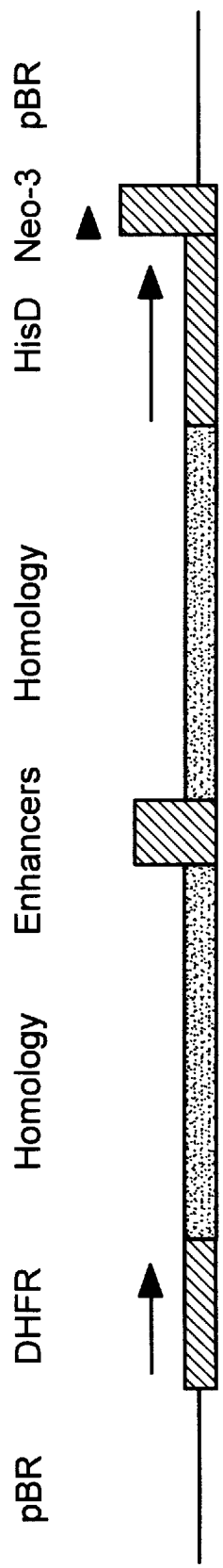
Figure 2B:
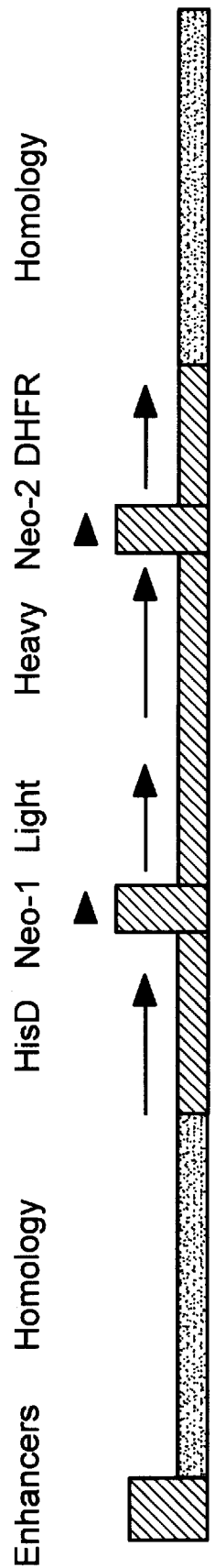
FIG. 2(b) shows a linearized version of Molly, after digestion with the restriction enzymes Kpn1 and Pac1. This linearized form was used for transfection.
Figure 3:
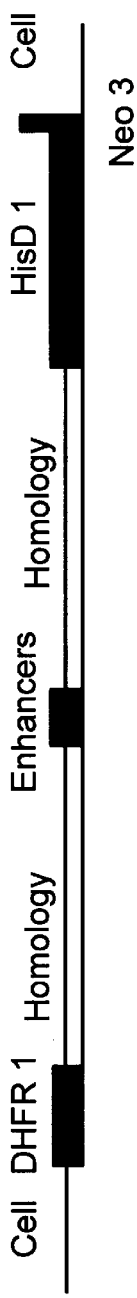
FIG. 3 depicts the potential alignment between Desmond sequences integrated into the CHO genome, and incoming targeting Molly sequences. One potential arrangement of Molly integrated into Desmond after homologous recombination is also presented.
Figure 3:
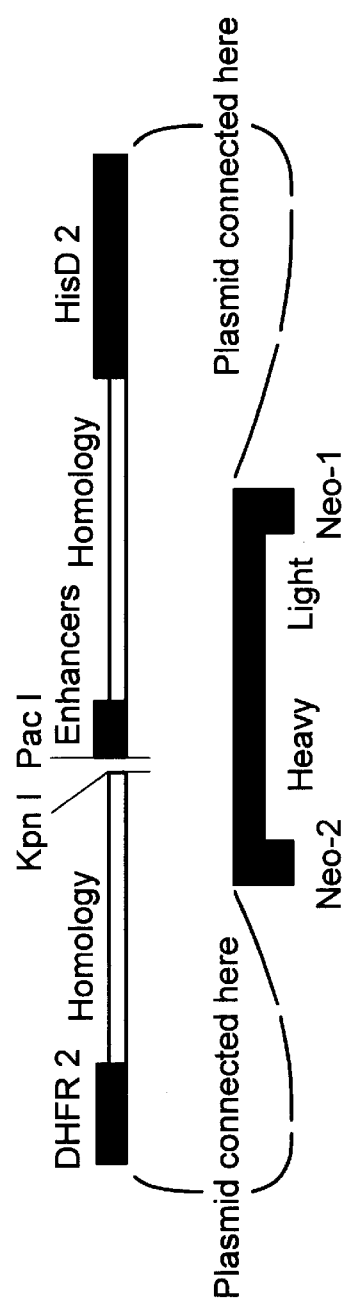
Figure 3:
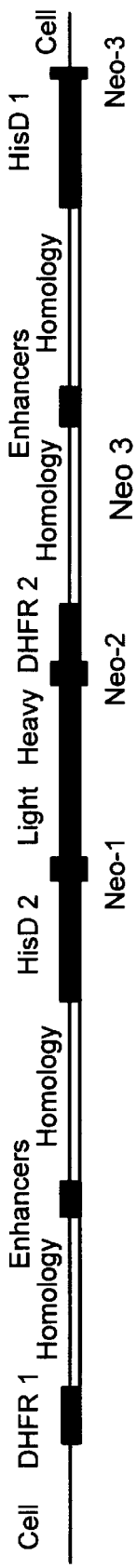

FIG. 1 depicts the arrangement of these DNA elements in the marker plasmid "Desmond". FIG. 2 depicts the arrangement of these elements in the first targeting plasmid, "Molly". FIG. 3 illustrates the possible arrangement in the CHO genome, of the various DNA elements after targeting and integration of Molly DNA into Desmond marked CHO cells. FIG. 7 depicts the targeting plasmid "Mandy."

Construction of the marking and targeting plasmids from the above listed DNA elements was carried out following conventional cloning techniques (see, e.g., Molecular Cloning, A Laboratory Manual, J. Sambrook et al, 1987, Cold Spring Harbor Laboratory Press, and Current Protocols in Molecular Biology, F. M. Ausubel et al, eds., 1987, John Wiley and Sons). All plasmids were propagated and maintained in *E. coli* XLI blue (Stratagene, cat. # 200236). Large scale plasmid preparations were prepared using Promega Wizard Maxiprep DNA Purification System®, according to the manufacturer's directions.

EXAMPLE 2

Construction of a Marked CHO Cell Line

1. Cell Culture and Transfection Procedures to Produced Marked CHO Cell Line

Marker plasmid DNA was linearized by digestion overnight at 37° C. with Bst1107I. Linearized vector was ethanol precipitated and resuspended in sterile TE to a concentration of 1 mg/ml. Linearized vector was introduced into DHFR- Chinese hamster ovary cells (CHO cells) DG44 cells (Urlaub et al, *Som. Cell and Mol. Gen.*, 12:555–566 (1986)) by electroporation as follows.

Exponentially growing cells were harvested by centrifugation, washed once in ice cold SBS (sucrose buffered solution, 272 mM sucrose, 7 mM sodium phosphate, pH 7.4, 1 mM magnesium chloride) then resuspended in SBS to a concentration of $10^7$ cells/ml. After a 15 minute incubation on ice, 0.4 ml of the cell suspension was mixed with 40 μg linearized DNA in a disposable electroporation cuvette. Cells were shocked using a BTX electrocell manipulator (San Diego, Calif.) set at 230 volts, 400 microfaraday capacitance, 13 ohm resistance. Shocked cells were then mixed with 20 ml of prewarmed CHO growth media (CHO-S-SFMII, Gibco/BRL, catalog # 31033-012) and plated in 96 well tissue culture plates. Forty eight hours after electroporation, plates were fed with selection media (in the case of transfection with Desmond, selection media is CHO- S-SFMII without hypoxanthine or thymidine, supplemented with 2 mM Histidinol (Sigma catalog # H6647)). Plates were maintained in selection media for up to 30 days, or until some of the wells exhibited cell growth. These cells were then removed from the 96 well plates and expanded ultimately to 120 ml spinner flasks where they were maintained in selection media at all times.

EXAMPLE 3

Characterization of Marked CHO Cell Lines (a) Southern Analysis

Figure 4:
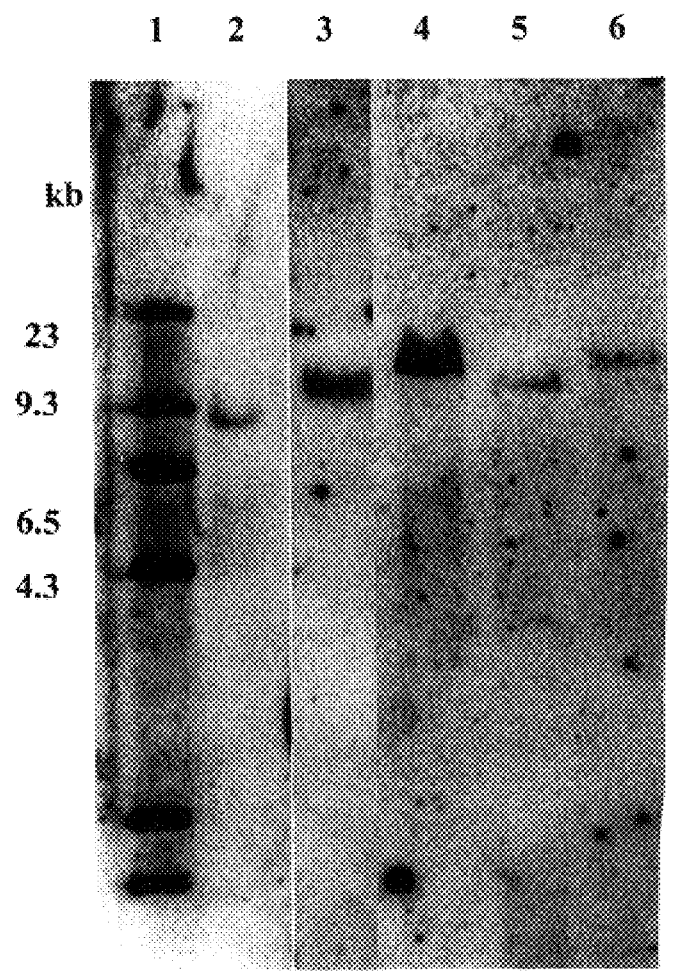
FIG. 4 shows a Southern analysis of single copy Desmond clones. Samples are as follows:
Lane 1: λHindIII DNA size marker
Lane 2: Desmond clone 10F3
Lane 3: Desmond clone 10C12
Lane 4: Desmond clone 15C9
Lane 5: Desmond clone 14B5
Lane 6: Desmond clone 9B2

Genomic DNA was isolated from all stably growing Desmond marked CHO cells. DNA was isolated using the Invitrogen Easy® DNA kit, according to the manufacturer's directions. Genomic DNA was then digested with HindIII overnight at 37° C., and subjected to Southern analysis using a PCR generated digoxygenin labelled probe specific to the DHFR gene. Hybridizations and washes were carried out using Boehringer Mannheim's DIG easy hyb (catalog # 1603 558) and DIG Wash and Block Buffer Set (catalog # 1585 762) according to the manufacturer's directions. DNA samples containing a single band hybridizing to the DHFR probe were assumed to be Desmond clones arising from a single cell which had integrated a single copy of the plasmid. These clones were retained for further analysis. Out of a total of 45 HisD resistant cell lines isolated, only 5 were single copy integrants. FIG. 4 shows a Southern blot containing all 5 of these single copy Desmond clones. Clone names are provided in the figure legend.

(b) Northern Analysis

Figure 5:
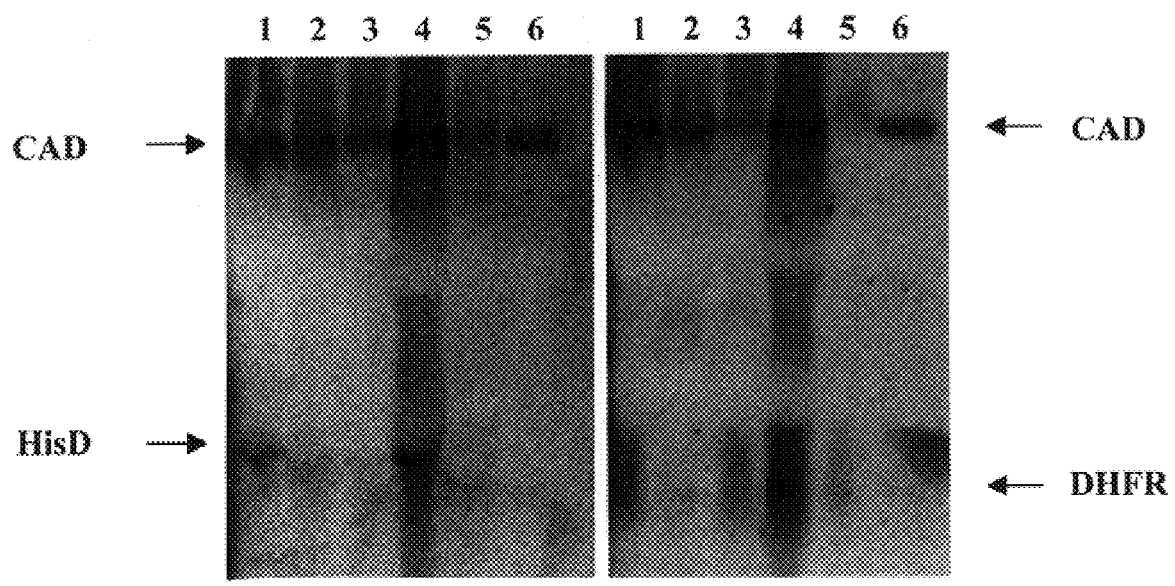
FIG. 5 shows a Northern analysis of single copy Desmond clones. Samples are as follows: Panel A: northern probed with CAD and DHFR probes, as indicated on the figure. Panel B: duplicate northern, probed with CAD and HisD probes, as indicated. The RNA samples loaded in panels A and B are as follows: Lane 1: clone 9B2, lane 2; clone 10C12, lane 3; clone 14B5, lane 4; clone 15C9, lane 5; control RNA from CHO transfected with a HisD and DHFR containing plasmid, lane 6; untransfected CHO.

Total RNA was isolated from all single copy Desmond clones using TRIzol reagent (Gibco/BRL cat # 15596-026) according to the manufacturer's directions. 10–20 µg RNA from each clone was analyzed on duplicate formaldehyde gels. The resulting blots were probed with PCR generated digoxygenin labelled DNA probes to (i) DHFR message, (ii) HisD message and (iii) CAD message. CAD is a trifunctional protein involved in uridine biosynthesis (Wahl et al, *J. Biol. Chem.*, 254, 17:8679–8689 (1979)), and is expressed equally in all cell types. It is used here as an internal control to help quantitate RNA loading. Hybridizations and washes were carried out using the above mentioned Boehringer Mannheim reagents. The results of the Northern analysis are shown in FIG. 5. The single copy Desmond clone exhibiting the highest levels of both the His D and DHFR message is clone 15C9, shown in lane 4 in both panels of the figure. This clone was designated as the "marked cell line" and used in future targeting experiments in CHO, examples of which are presented in the following sections.

EXAMPLE 4

Expression of Anti-CD20 Antibody in Desmond Marked CHO Cells

C2B8, a chimeric antibody which recognizes B-cell surface antigen CD20, has been cloned and expressed previously in our laboratory. (Reff et al, *Blood*, 83:434–45 (1994)). A 4.1 kb DNA fragment comprising the C2B8 light and heavy chain genes, along with the necessary regulatory elements (eukaryotic promoter and polyadenylation signals) was inserted into the artificial intron created between exons 1 and 2 of the neo gene contained in a pBR derived cloning vector. This newly generated 5 kb DNA fragment (comprising neo exon 1, C2B8 and neo exon 2) was excised and used to assemble the targeting plasmid Molly. The other DNA elements used in the construction of Molly are identical to those used to construct the marking plasmid Desmond, identified previously. A complete map of Molly is shown in FIG. 2.

The targeting vector Molly was linearized prior to transfection by digestion with Kpn1 and Pac1, ethanol precipitated and resuspended in sterile TE to a concentration of 1.5 mg/mL. Linearized plasmid was introduced into exponentially growing Desmond marked cells essentially as described, except that 80 µg DNA was used in each electroporation. Forty eight hours postelectroporation, 96 well plates were supplemented with selection medium—CHO-SSFMII supplemented with 400 µg/mL Geneticin (G418, Gibco/BRL catalog # 10131-019). Plates were maintained in selection medium for up to 30 days, or until cell growth occurred in some of the wells. Such growth was assumed to be the result of clonal expansion of a single G418 resistant cell. The supernatants from all G418 resistant wells were assayed for C2B8 production by standard ELISA techniques, and all productive clones were eventually expanded to 120 mL spinner flasks and further analyzed.

Characterization of Antibody secreting Targeted Cells

Figure 6:
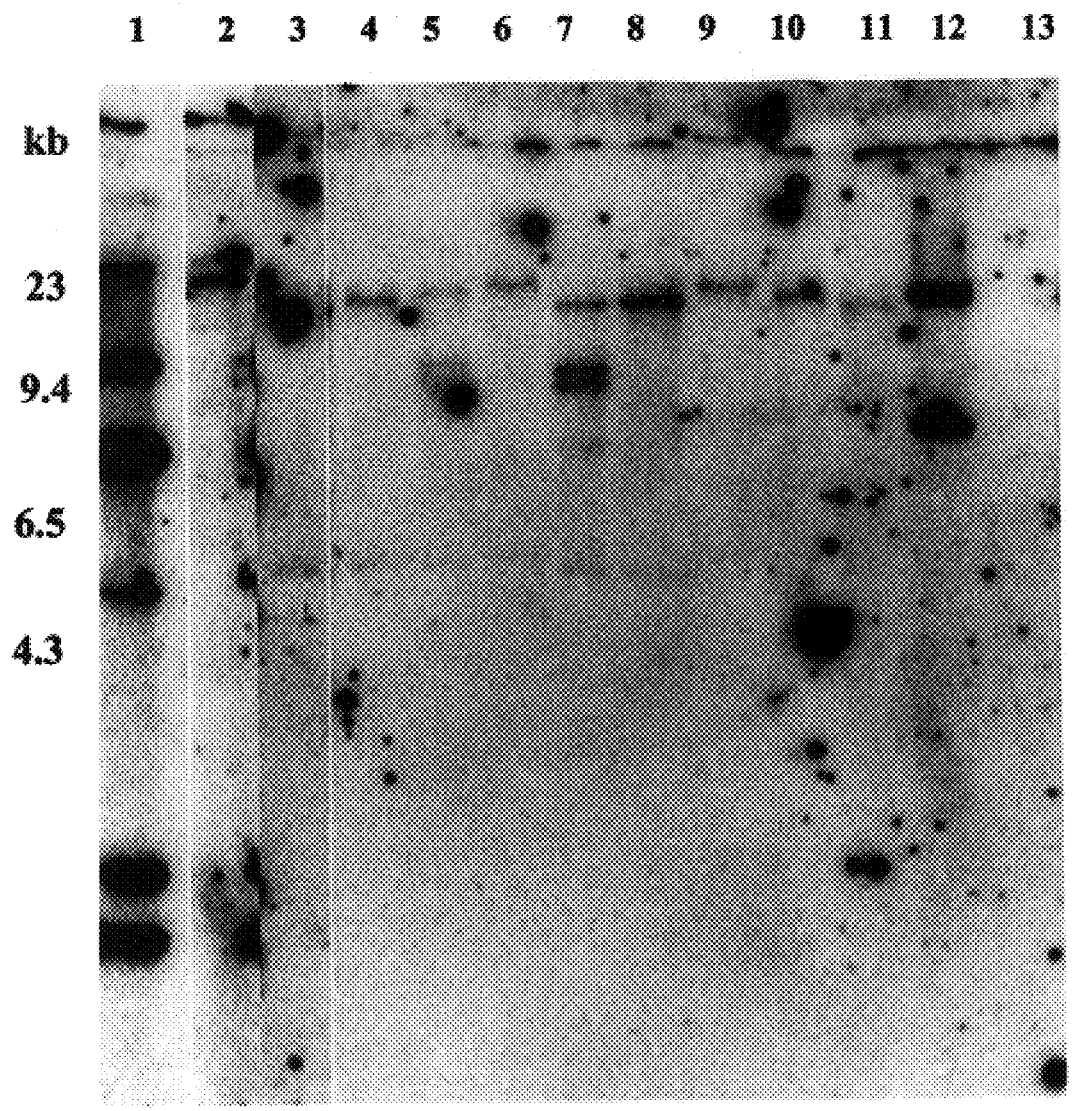
FIG. 6 shows a Southern analysis of clones resulting from the homologous integration of Molly into Desmond. Samples are as follows:
Lane 1: λHindIII DNA size markers, Lane 2: 20F4, lane 3; 5F9, lane 4; 21C7, lane 5; 24G2, lane 6; 25E1, lane 7; 28C9, lane 8; 29F9, lane 9; 39G11, lane 10; 42F9, lane 11; 50G10, lane 12; Molly plasmid DNA, linearized with BglII (top band) and cut with BglII and KpnI (lower band), lane 13; untransfected Desmond.

A total of 50 electroporations with Molly targeting plasmid were carried out in this experiment, each of which was plated into separate 96 well plates. A total of 10 viable, anti-CD20 antibody secreting clones were obtained and expanded to 120 ml spinner flasks. Genomic DNA was isolated from all clones, and Southern analyses were subsequently performed to determine whether the clones represented single homologous recombination events or whether additional random integrations had occurred in the same cells. The methods for DNA isolation and Southern hybridization were as described in the previous section. Genomic DNA was digested with EcoRI and probed with a PCR generated digoxygenin labelled probe to a segment of the CD20 heavy chain constant region. The results of this Southern analysis are presented in FIG. 6. As can be seen in the figure, 8 of the 10 clones show a single band hybridizing to the CD20 probe, indicating a single homologous recombination event has occurred in these cells. Two of the ten, clones 24G2 and 28C9, show the presence of additional band(s), indicative of an additional random integration elsewhere in the genome.

We examined the expression levels of anti-CD20 antibody in all ten of these clones, the data for which is shown in Table 1, below.

TABLE 1

| Expression Level of Anti-CD20 Secreting Homologous Integrants | |
|---|---|
| Clone | Anti-CD20, pg/c/d |
| 20F4 | 3.5 |
| 25E1 | 2.4 |
| 42F9 | 1.8 |
| 39G11 | 1.5 |
| 21C7 | 1.3 |
| 50G10 | 0.9 |
| 29F9 | 0.8 |
| 5F9 | 0.3 |
| 28C9* | 4.5 |
| 24G2* | 2.1 |

*These clones contained additional randomly integrated copies of anti-CD20. Expression levels of these clones therefore reflect a contribution from both the homologous and random sites.

Expression levels are reported as picogram per cell per day (pg/c/d) secreted by the individual clones, and represented the mean levels obtained from three separate ELISAs on samples taken from 120 mL spinner flasks.

As can be seen from the data, there is a variation in antibody secretion of approximately ten fold between the highest and lowest clones. This was somewhat unexpected as we anticipated similar expression levels from all clones due to the fact the anti-CD20 genes are all integrated into the same Desmond marked site. Nevertheless, this observed range in expression extremely small in comparison to that seen using any traditional random integration method or with our translationally impaired vector system.

Clone 20F4, the highest producing single copy integrant was selected for further study. Table 2 (below) presents ELISA and cell culture data from seven day production runs of this clone.

TABLE 2

7 Day Production Run Data for 20F4

| Day | % Viable | Viable/ml (× 10⁵) | T × 2 (hr) | mg/L | pg/c/d |
|---|---|---|---|---|---|
| 1 | 96 | 3.4 | 31 | 1.3 | 4.9 |
| 2 | 94 | 6 | 29 | 2.5 | 3.4 |
| 3 | 94 | 9.9 | 33 | 4.7 | 3.2 |
| 4 | 90 | 17.4 | 30 | 6.8 | 3 |
| 5 | 73 | 14 | | 8.3 | |
| 6 | 17 | 3.5 | | 9.5 | |

Clone 20F4 was seeded at 2 × 10⁵ ml in a 120 ml spinner flask on day 0. On the following six days, cell counts were taken, doubling times calculated and 1 ml samples of supernatant removed from the flask and analyzed for secreted anti-CD20 by ELISA.

This clone is secreting on average, 3–5 pg antibody/cell/day, based on this ELISA data. This is the same level as obtained from other high expressing single copy clones obtained previously in our laboratory using the previously developed translationally impaired random integration vectors. This result indicates the following:

(1) that the site in the CHO genome marked by the Desmond marking vector is highly transcriptionally active, and therefore represents an excellent site from which to express recombinant proteins, and (2) that targeting by means of homologous recombination can be accomplished using the subject vectors and occurs at a frequency high enough to make this system a viable and desirable alternative to random integration methods.

To further demonstrate the efficacy of this system, we have also demonstrated that this site is amplifiable, resulting in even higher levels of gene expression and protein secretion. Amplification was achieved by plating serial dilutions of 20F4 cells, starting at a density of 2.5×10⁴ cells/ml, in 96 well tissue culture dishes, and culturing these cells in media (CHO-SSFMII) supplemented with 5, 10, 15 or 20 nM methotrexate. Antibody secreting clones were screened using standard ELISA techniques, and the highest producing clones were expanded and further analyzed. A summary of this amplification experiment is presented in Table 3 below.

TABLE 3

Summary of 20F4 Amplification

| nM MTX | # Wells Assayed | Expression Level mg/l 96 well | # Wells Expanded | Expression Level pg/c/d from spinner |
|---|---|---|---|---|
| 10 | 56 | 3–13 | 4 | 10–15 |
| 15 | 27 | 2–14 | 3 | 15–-18 |
| 20 | 17 | 4–11 | 1 | ND |

Methotrexate amplification of 20F4 was set up as described in the text, using the concentrations of methotrexate indicated in the above table. Supernatants from all surviving 96 well colonies were assayed by ELISA, and the range of anti-CD20 expressed by these clones is indicated in column 3. Based on these results, the highest producing clones were expanded to 120 ml spinners and severalELISAs conducted on the spinner supernatants to determine the pg/cell/day expression levels, reported in column 5.

The data here clearly demonstrates that this site can be amplified in the presence of methotrexate. Clones from the 10 and 15 nM amplifications were found to produce on the order of 15–20 pg/cell/day.

A 15 nM clone, designated 20F4-15A5, was selected as the highest expressing cell line. This clone originated from a 96 well plate in which only 22 wells grew, and was therefore assumed to have arisen from a single cell. A 15 nM clone, designated 20F4-15A5, was selected as the highest expressing cell line. This clone originated from a 96 well plate in which only 22 wells grew, and was therefore assumed to have arisen from a single cell. The clone was then subjected to a further round of methotrexate amplification. As described above, serial dilutions of the culture were plated into 96 well dishes and cultured in CHO-SS-FMII medium supplemented with 200, 300 or 400 nM methotrexate. Surviving clones were screened by ELISA, and several high producing clones were expanded to spinner cultures and further analyzed. A summary of this second amplification experiment is presented in Table 4.

TABLE 4

Summary of 20F4-15A5 Amplification

| nM MTX | # Wells Assayed | Expression Level mg/l 96 well | # Wells Expanded | Expression Level pg/c/d, spinner |
|---|---|---|---|---|
| 200 | 67 | 23–70 | 1 | 50–60 |
| 250 | 86 | 21–70 | 4 | 55–60 |
| 300 | 81 | 15–75 | 3 | 40–50 |

Methotrexate amplifications of 20F4-15A5 were set up and assayed as described in the text. The highest producing wells, the numbers of which are indicated in column 4, were expanded to 120 ml spinner flasks. The expression levels of the cell lines derived from these wells is recorded as pg/c/d in column 5.

The highest producing clone came from the 250 nM methotrexate amplification. The 250 nM clone, 20F4-15A5-250A6 originated from a 96 well plate in which only wells grew, and therefore is assumed to have arisen from a single cell. Taken together, the data in Tables 3 and 4 strongly indicates that two rounds of methotrexate amplification are sufficient to reach expression levels of 60 pg/cell/day, which is approaching the maximum secretion capacity of immunoglobulin in mammalian cells (Reff, M. E., Curr. Opin. Biotech., 4:573–576 (1993)). The ability to reach this secretion capacity with just two amplification steps further enhances the utility of this homologous recombination system. Typically, random integration methods require more than two amplification steps to reach this expression level and are generally less reliable in terms of the ease of amplification. Thus, the homologous system offers a more efficient and time saving method of achieving high level gene expression in mammalian cells.

EXAMPLE 5

Expression of Anti-Human CD23 Antibody in Desmond Marked CHO Cells

CD23 is low affinity IgE receptor which mediates binding of IgE to B and T lymphocytes (Sutton, B. J., and Gould, H. J., Nature, 366:421–428 (1993)). Anti-human CD23 monoclonal antibody 5E8 is a human gamma-1 monoclonal antibody recently cloned and expressed in our laboratory. This antibody is disclosed in commonly assigned Ser. No. 08/803,085, filed on Feb. 20, 1997.

The heavy and light chain genes of 5E8 were cloned into the mammalian expression vector NSKG1, a derivative of the vector NEOSPLA (Barnett et al, in Antibody Expression and Engineering, H. Y Yang and T. Imanaka, eds., pp 27–40 (1995)) and two modifications were then made to the genes. We have recently observed somewhat higher secretion of immunoglobulin light chains compared to heavy chains in other expression constructs in the laboratory (Reff et al, 1997, unpublished observations). In an attempt to compensate for this deficit, we altered the 5E8 heavy chain gene by the addition of a stronger promoter/enhancer element immediately upstream of the start site. In subsequent steps, a 2.9 kb DNA fragment comprising the 5E8 modified light and heavy chain genes was isolated from the N5KG1 vector and inserted into the targeting vector Mandy. Preparation of 5E8-containing Molly and electroporation into Desmond 15C9 CHO cells was essentially as described in the preceding section.

One modification to the previously described protocol was in the type of culture medium used. Desmond marked CHO cells were cultured in protein-free CD-CHO medium (Gibco-BRL, catalog # AS21206) supplemented with 3 mg/L recombinant insulin (3 mg/mL stock, Gibco-BRL, catalog # AS22057) and 8 mM L-glutamine (200 mM stock, Gibco-BRL, catalog # 25030-081). Subsequently, transfected cells were selected in the above medium supplemented with 400 μg/mL geneticin. In this experiment, 20 electroporations were performed and plated into 96 well tissue culture dishes. Cells grew and secreted anti-CD23 in a total of 68 wells, all of which were assumed to be clones originating from a single G418 cell. Twelve of these wells were expanded to 120 ml spinner flasks for further analysis. We believe the increased number of clones isolated in this experiment (68 compared with 10 for anti-CD20 as described in Example 4) is due to a higher cloning efficiency and survival rate of cells grown in CD-CHO medium compared with CHO-SS-FMII medium. Expression levels for those clones analyzed in spinner culture ranged from 0.5–3 pg/c/d, in close agreement with the levels seen for the anti-CD20 clones. The highest producing anti-CD23 clone, designated 4H12, was subjected to methotrexate amplification in order to increase its expression levels. This amplification was set up in a manner similar to that described for the anti-CD20 clone in Example 4. Serial dilutions of exponentially growing 4H12 cells were plated into 96 well tissue culture dishes and grown in CD-CHO medium supplemented with 3 mg/L insulin, 8 mM glutamine and 30, 35 or 40 nM methotrexate. A summary of this amplification experiment is presented in Table 5.

TABLE 5

Summary of 2H12 Amplification

| nM MTX | # Wells Assayed | Expression Level mg/l 96 well | # Wells Expanded | Expression Level pg/c/d from spinner |
|---|---|---|---|---|
| 30 | 100 | 6–24 | 8 | 10–25 |
| 35 | 64 | 4–27 | 2 | 10–15 |
| 40 | 96 | 4–20 | 1 | ND |

The highest expressing clone obtained was a 30 nM clone, isolated from a plate on which 22 wells had grown. This clone, designated 4H12-30G5, was reproducibly secreting 18–22 pg antibody per cell per day. This is the same range of expression seen for the first amplification of the anti CD20 clone 20F4 (clone 20F4-15A5 which produced 15–18 pg/c/d, as described in Example 4). This data serves to further support the observation that amplification at this marked site in CHO is reproducible and efficient. A second amplification of this 30 nM cell line is currently underway. It is anticipated that saturation levels of expression will be achievable for the anti-CD23 antibody in just two amplification steps, as was the case for anti-CD20.

EXAMPLE 6

Expression of Immunoadhesin in Desmond Marked CHO Cells

CTLA-4, a member of the Ig superfamily, is found on the surface of T lymphocytes and is thought to play a role in antigen-specific T-cell activation (Dariavach et al, *Eur. J. Immunol.*, 18:1901–1905 (1988); and Linsley et al, *J. Exp. Med.*, 174:561–569 (1991)). In order to further study the precise role of the CTLA-4 molecule in the activation pathway, a soluble fusion protein comprising the extracellular domain of CTLA-4 linked to a truncated form of the human IgGl constant region was created (Linsley et al (Id.). We have recently expressed this CTLA-4 Ig fusion protein in the mammalian expression vector BLECH1, a derivative of the plasmid NEOSPLA (Barnett et al, in Antibody Expression and Engineering, H. Y Yang and T. Imanaka, eds., pp 27–40 (1995)). An 800 bp fragment encoding the CTLA-4 Ig was isolated from this vector and inserted between the SacII and BglII sites in Molly.

Preparation of CTLA-4Ig-Molly and electroporation into Desmond clone 15C9 CHO cells was performed as described in the previous example relating to anti-CD20. Twenty electroporations were carried out, and plated into 96 well culture dishes as described previously. Eighteen CTLA-4 expressing wells were isolated from the 96 well plates and carried forward to the 120 ml spinner stage. Southern analyses on genomic DNA isolated from each of these clones were then carried out to determine how many of the homologous clones contained additional random integrants. Genomic DNA was digested with BglII and probed with a PCR generated digoxygenin labelled probe to the human IgG1 constant region. The results of this analysis indicated that 85% of the CTLA-4 clones are homologous integrants only; the remaining 15% contained one additional random integrant. This result corroborates the findings from the expression of anti-CD20 discussed above, where 80% of the clones were single homologous integrants. Therefore, we can conclude that this expression system reproducibly yields single targeted homologous integrants in at least 80% of all clones produced.

Expression levels for the homologous CTlA4-Ig clones ranged from 8–12 pg/cell/day. This is somewhat higher than the range reported for anti-CD20 antibody and anti-CD23 antibody clones discussed above. However, we have previously observed that expression of this molecule using the intronic insertion vector system also resulted in significantly higher expression levels than are obtained for immunoglobulins. We are currently unable to provide an explanation for this observation.

EXAMPLE 7

Targeting Anti-CD20 to an alternate Desmond Marked CHO Cell Line

As we described in a preceding section, we obtained 5 single copy Desmond marked CHO cell lines (see FIGS. 4 and 5). In order to demonstrate that the success of our targeting strategy is not due to some unique property of Desmond clone 15C9 and limited only to this clone, we introduced anti-CD20 Molly into Desmond clone 9B2 (lane 6 in FIG. 4, lane 1 in FIG. 5). Preparation of Molly DNA and electroporation into Desmond 9B2 was exactly as described in the previous example pertaining to anti-CD20. We obtained one homologous integrant from this experiment. This clone was expanded to a 120 ml spinner flask, where it produced on average 1.2 pg anti-CD20/cell/day. This is considerably lower expression than we observed with Molly targeted into Desmond 15C9. However, this was the anticipated result, based on our northern analysis of the Desmond clones. As can be seen in FIG. 5, mRNA levels from clone 9B2 are considerably lower than those from 15C9, indicating the site in this clone is not as transcriptionally active as that in 15C9. Therefore, this experiment not only demonstrates the reproducibility of the system—presumably any marked Desmond site can be targeted with Molly—it also confirms the northern data that the site in Desmond 15C9 is the most transcriptionally active.

From the foregoing, it will be appreciated that, although specific embodiments of the invention have been described herein for purposes of illustration, various modifications may be made without diverting from the scope of the invention. Accordingly, the invention is not limited by the appended claims.

What is claimed is:

1. A method for inserting a DNA at a target site in the genome of a desired cell which comprises the following steps:
   (i) transfecting or transforming a cell with a first plasmid ("marker plasmid") comprising the following sequences:
      (a) a first DNA fragment which comprises a region of DNA that is heterologous to the cell genome which when integrated in the cell genome provides a unique site for homologous recombination;
      (b) a second DNA fragment which comprises a region encoding a portion of a first selectable marker protein, wherein said second DNA fragment is distinct from said first DNA fragment and does not function as a site for homologous recombination; and
      (c) a third DNA fragment which comprises a region encoding at least one other selectable marker protein, wherein said at least one other selectable marker protein is different than the first selectable marker protein, and provides for selection of a cell in which said marker plasmid is integrated in the genome of the cell;
   (ii) selecting a cell which contains the marker plasmid integrated in its genome by screening for expression of a selectable marker protein encoded by said third DNA fragment;
   (iii) transfecting or transforming said selected cell with a second plasmid ("target plasmid") which comprises the following sequences:
      (a) a first DNA fragment which comprises a region of DNA that is identical or is sufficiently homologous to said unique site for homologous recombination in the marker plasmid such that this region of DNA can recombine with said site via homologous recombination;
      (b) a second DNA fragment encoding a portion of the first selectable marker protein not contained in the marker plasmid, wherein an active first selectable marker protein is only produced if said second DNA fragment of the target plasmid is expressed in association with said second DNA fragment encoding a portion of a first selectable marker protein of the marker plasmid; and
   (iv) selecting cells which contain the target plasmid integrated within the unique site for homologous recombination of the marker plasmid by screening for the expression of the first selectable marker protein.

2. The method of claim 1, wherein said DNA fragment encoding a portion of the first selectable marker protein of said target or marker plasmid comprises one or more exons of a gene encoding said first selectable marker protein.

3. The method of claim 2, wherein the target plasmid comprises the remaining exons of a gene encoding said first selectable marker protein not contained in said marker plasmid.

4. The method of claim 3, wherein at least one DNA encoding a desired protein is inserted adjacent to one of said exons.

5. The method of claim 4, wherein a DNA encoding a dominant selectable marker protein is further inserted adjacent to one of said exons to provide for co-amplification of the DNA encoding the desired protein.

6. The method of claim 3, wherein the first selectable marker protein is selected from the group consisting of neomycin phosphotransferase, histidinol dehydrogenase, dihydrofolate reductase, hygromycin phosphotransferase, herpes simplex virus thymidine kinase, adenosine deaminase, glutamine synthetase, and hypoxanthine-guanine phosphoribosyl transferase.

7. The method of claim 4, wherein the desired protein is a mammalian protein.

8. The method of claim 7, wherein the protein is an immunoglobulin.

9. The method of claim 1, which further comprises determining the levels of expression of said at least one other selectable marker protein of the marker plasmid prior to integration of the target vector.

10. The method of claim 9, wherein said at least one other selectable marker protein is a dominant selectable marker protein selected from the group consisting of histidinol dehydrogenase, herpes simplex thymidine kinase, hydromycin phosphotransferase, adenosine deaminase, and glutamine synthetase.

11. The method of claim 1, wherein the cell is selected from the group consisting of Chinese hamster ovary (CHO) cells, myeloma cells, baby hamster kidney cells, COS cells, NSO cells, HeLa cells, and NIH 3T3 cells.

12. The method of claim 11, wherein the cell is a CHO cell.

13. The method of claim 1, wherein the second DNA fragment of said marker plasmid comprises the third exon of a neomycin phosphotransferase gene and the second DNA fragment of said target plasmid comprises the first two exons of the neomycin phosphotransferase gene.

14. The method of claim 1, wherein the marker plasmid further comprises a rare restriction endonuclease sequence which is inserted within the unique site for homologous recombination.

15. The method of claim 1, wherein the unique site for homologous recombination is a bacterial DNA, a viral DNA, or a synthetic DNA.

16. The method of claim 1, wherein the unique site for homologous recombination is at least 300 nucleotides.

17. The method of claim 16, wherein the unique site for homologous recombination ranges in size from about 300 nucleotides to 20 kilobases.

18. The method of claim 17, wherein the unique site for homologous recombination ranges in size from 2 to 10 kilobases.

19. The method of claim 1, wherein the DNA encoding the first selectable marker protein is split into at least three exons, wherein at least one exon is comprised in the marker plasmid and the remaining exons, excluding said at least one exon, are comprised in the target plasmid.

20. The method of claim 1, wherein the unique site for homologous recombination is a bacterial DNA, an insect DNA, a viral DNA, or a synthetic DNA.

21. The method of claim 20, wherein the unique site for homologous recombination does not contain any functional genes.

22. A kit for inserting a DNA at a target site in the genome of a cell which comprises at least the following:
   (i) a first plasmid ("marker plasmid") comprising at least the following sequences:
      (a) a first DNA fragment that comprises a region of DNA that is heterologous to the cell genome which when integrated in the cell genome provides a unique site for homologous recombination;
   (b) a second DNA fragment that comprises a region encoding a portion of a first selectable marker protein, wherein said second DNA fragment is distinct from said first DNA fragment, and does not function as a site for homologous recombination; and
   (c) a third DNA fragment which comprises a region encoding at least one other selectable marker protein, wherein said at least one other selectable marker protein is different from the first selectable marker protein, ad provides for selection of a cell in which said marker plasmid is integrated in the genome of the cell; and
(ii) a second plasmid ("target plasmid") which comprises at least the following sequences:
   (a) a first DNA fragment that comprises a region of DNA that is identical or is sufficiently homologous to said unique site for homologous recombination in the marker plasmid such that this region of DNA can recombine with said site via homologous recombination;
   (b) a second DNA comprising a DNA fragment encoding a portion of the first selectable marker protein not contained in the marker plasmid, wherein an active first selectable marker protein is only produced if said second DNA fragment of the target plasmid is expressed in association with said second DNA fragment encoding a portion of a first selectable marker protein of the marker plasmid.

23. The kit of claim 22, wherein each DNA fragment encoding a portion of the first selectable marker protein of said marker or target plasmid comprises one or more exons of a gene encoding said first selectable marker protein.

24. The kit of claim 23, wherein the marker or target plasmid comprises the remaining exons of a gene encoding the first selectable marker protein not contained in said marker plasmid.

25. The kit of claim 24, wherein at least one DNA encoding a desired protein is inserted adjacent to one of said exons.

26. The kit of claim 24, wherein a DNA encoding a dominant selectable marker protein is further inserted adjacent to one of said exons to provide for co-amplification of the DNA encoding the desired protein.

27. The kit of claim 26, wherein the first dominant selectable marker protein is selected from the group consisting of neomycin phosphotransferase, histidinol dehydrogenase, dihydrofolate reductase, hygromycin phosphotransferase, herpes simplex virus thymidine kinase, adenosine deaminase, glutamine synthetase, and hypoxanthine-guanine phosphoribosyl transferase.

28. The kit of claim 25, wherein the desired protein is a mammalian protein.

29. The kit of claim 28, wherein the protein is an immunoglobulin.

30. The kit of claim 22, wherein said at least one other selectable marker protein of the marker plasmid is a dominant selectable marker protein selected from the group consisting of histidinol dehydrogenase, herpes simplex thymidine kinase, hydromycin phosphotransferase, adenosine deaminase, and glutamine synthetase.

31. The kit of claim 22, which provides for insertion of a DNA at a targeted site in the genome of a cell selected from the group consisting of Chinese hamster ovary (CHO) cells, myeloma cells, baby hamster kidney cells, COS cells, NSO cells, HeLa cells, and NIH 3T3 cells.

32. The kit of claim 31, wherein the cell is a CHO cell.

33. The kit of claim 22, wherein the second DNA fragment of said marker plasmid comprises the third exon of a neomycin phosphotransferase gene and the second DNA fragment of said target plasmid comprises the first two exons of the neomycin phosphotransferase gene.

34. The kit of claim 22, wherein the marker plasmid further comprises a rare restriction endonuclease sequence which is inserted within the unique site for homologous recombination.

35. The kit of claim 22, wherein said unique site for homologous recombination is a bacterial DNA, a viral DNA, or a synthetic DNA.

36. The kit of claim 22, wherein said unique site for homologous recombination is at least 300 nucleotides.

37. The kit of claim 36, wherein said unique site for homologous recombination ranges in size from about 300 nucleotides to 20 kilobases.

38. The kit of claim 37, wherein said unique site for homologous recombination ranges in size from 2 to 10 kilobases.

39. The kit of claim 22, wherein the DNA encoding the fist selectable marker protein is split into at least three exons, wherein at least one exon is contained in the target plasmid and the remaining exons, excluding said at least one exon, are contained in the marker plasmid.

40. The kit of claim 22, wherein said unique site for homologous recombination is a bacterial DNA.

41. The kit of claim 40, wherein said unique site for homologous recombination does not contain any functional genes.

42. A cell produced according to claim 1.

43. The cell of claim 42, which is a mammalian cell.

44. The cell of claim 42, wherein said cell is selected from the group consisting of Chinese hamster ovary (CHO) cells, myeloma cells, baby hamster kidney cells, COS cells, NSO cells, HeLa cells, and NIH 3T3 cells.

45. The cell of claim 44, which is a CHO cell.

* * * * *

UNITED STATES PATENT AND TRADEMARK OFFICE
CERTIFICATE OF CORRECTION

PATENT NO. : 5,998,144
DATED : December 7, 1999
INVENTOR(S) : REFF et al

It is certified that error appears in the above-identified patent and that said Letters Patent is hereby corrected as shown below:

COL. 21, line 12, delete "ad" and insert therefor --and--;

COL. 22, line 37, delete "fist" and insert therefor --first--.

Signed and Sealed this

Thirteenth Day of March, 2001

Attest:

NICHOLAS P. GODICI

Attesting Officer

Acting Director of the United States Patent and Trademark Office